(12) United States Patent
Dunn et al.

(10) Patent No.: US 7,608,410 B2
(45) Date of Patent: Oct. 27, 2009

(54) METHOD OF IMPROVING T CELL RECEPTORS

(75) Inventors: Steven Mark Dunn, Abingdon (GB); Yi Li, Abingdon (GB); Jonathan Michael Boulter, Abingdon (GB); Lucy Boulter, legal representative, Abingdon (GB)

(73) Assignee: Immunocore Limited, Oxford (GB)

( * ) Notice: Subject to any disclaimer, the term of this patent is extended or adjusted under 35 U.S.C. 154(b) by 0 days.

(21) Appl. No.: 12/246,607

(22) Filed: Oct. 7, 2008

(65) Prior Publication Data

US 2009/0054257 A1 Feb. 26, 2009

Related U.S. Application Data

(63) Continuation of application No. 11/579,874, filed as application No. PCT/GB2005/001781 on May 10, 2005, now abandoned.

(30) Foreign Application Priority Data

| May 19, 2004 | (GB) | ................... | 0411125.8 |
| Sep. 3, 2004 | (GB) | ................... | 0419646.5 |

(51) Int. Cl.
  *G01N 33/53*  (2006.01)
  *C12N 15/00*  (2006.01)
  *C12N 7/01*  (2006.01)
  *C12Q 1/70*  (2006.01)

(52) U.S. Cl. .............................. 435/7.1; 435/5; 435/7.2; 435/471; 530/350; 530/668

(58) Field of Classification Search ........................ None
See application file for complete search history.

(56) References Cited

U.S. PATENT DOCUMENTS

| 6,759,243 B2 * | 7/2004 | Kranz et al. ............. 435/372.3 |
| 2002/0048578 A1 | 4/2002 | Waldmann |
| 2002/0058253 A1 | 5/2002 | Kranz |

FOREIGN PATENT DOCUMENTS

| EP | 1 118 661 A | 7/2001 |
| WO | WO 98/39482 A | 9/1998 |

OTHER PUBLICATIONS

Wu et al., (Nature, Aug 1, 2002; vol. 418, Iss.6897, p. 552-556).*
Manning et al. (J. Exp. Med., vol. 189, No. 3, Feb. 1, 1999 461-470).*
IPER and Written Opinion of the International Searching Authority for PCT/GB2005/001781, Nov. 2006.*
Janeway et al. Immunobiology New York and London: Garland Science; c2001; Figure 5.18.*
EP05741949 Applicant's response submitted on Sep. 13, 2007.*
Churchill et al., "Mapping the energy of superantigen *Staphylococcus enterotoxin* C3 recognition of an alpha/beta T cell receptor using alanine scanning mutagenesis" Journal of Experimental Medicine, vol. 191, No. 5, Mar. 6, 2000.
Kieke et al., "High affinity T cell receptors from yeast display libraries block T cell activation by superantigens" Journal of Molecular Biology, London, GB, vol. 307, No. 5, Apr. 13, 2001, pp. 1305-1315.
Holler et al., "In vitro evolution of a T cell receptor with high affinity for peptide/MHC" Proceedings of the National Academy of Sciences of USA, National Academy of Science, Washington, DC, US, vol. 97, No. 10, May 9, 2000, pp. 5387-5392.
Chlewicki et al., "High-affinity, peptide-specific T cell receptors can be generated by mutations in CDR1, CDR2 or CDR3" Journal of Molecular Biology, vol. 346, No. 1, Feb. 11, 2005, pp. 223-239.

* cited by examiner

*Primary Examiner*—Daniel C Gamett
(74) *Attorney, Agent, or Firm*—Banner & Witcoff, Ltd.

(57) ABSTRACT

A method of increasing the affinity and/or decreasing the off-rate of a given TCR specific for a given target pMHC, comprising creating a plurality of TCRs having an α chain CDR2 sequence and/or a β chain CDR2 sequence different from the corresponding CDR2 sequence(s) of the given TCR but having the same α and β CDR1 and CDR3 sequences as the given TCR, determining the affinity and/or off-rate of members of said plurality of TCRs for the target pMHC, and selecting one or more members having at least a 10-fold greater affinity for the target pMHC than the given TCR and/or a 10-fold slower off-rate for the target pMHC than the given TCR.

13 Claims, 18 Drawing Sheets

Figure 1a atgcaggaggygacacagattcctgcagctctgagtgtcccagaaggagaaaacttgg
ttctcaactgcagtttcactgatagcgctatttacaacctccagtggtttaggcagga
ccctgggaaaggtctcacatctctgttgcttattcagtcaagtcagagagagcaaaca
agtggaagacttaatgcctcgctggataaatcatcaggacgtagtactttatacattg
cagcttctcagcctggtgactcagccacctacctctgtgctgtgaggcccacatcagg
aggaagctacatacctacatttggaagaggaaccagccttattgttcatccgtatatc
cagaaccctgaccctgccgtgtaccagctgagagactctaaatccagtgacaagtctg
tctgcctattcaccgatttgattctcaaacaaatgtgtcacaaagtaaggattctga
tgtgtatatcacagacaaatgtgtgctagacatgaggtctatggacttcaagagcaac
agtgctgtggcctggagcaacaaatctgactttgcatgtgcaaacgccttcaacaaca
gcattattccagaagacaccttcttccccagcccagaaagttcctaa
(SEQ ID NO: 26)

Figure 1b atgggtgtcactcagaccccaaaattccaggtcctgaagacaggacagagcatgacac
tgcagtgtgcccaggatatgaaccatgaatacatgtcctggtatcgacaagacccagg
catggggctgaggctgattcattactcagttggtgctggtatcactgaccaaggagaa
gtccccaatggctacaatgtctccagatcaaccacagaggatttcccgctcaggctgc
tgtcggctgctccctcccagacatctgtgtacttctgtgccagcagttacgtcgggaa
caccggggagctgttttttggagaaggctctaggctgaccgtactggaggacctgaaa
aacgtgttcccacccgaggtcgctgtgtttgagccatcagaagcagagatctcccaca
cccaaaaggccacactggtgtgcctggccacaggcttctaccccgaccacgtggagct
gagctggtgggtgaatgggaaggaggtgcacagtggggtctgcacagacccgcagccc
ctcaaggagcagcccgccctcaatgactccagatacgctctgagcagccgcctgaggg
tctcggccaccttctggcaggaccccgcaaccacttccgctgtcaagtccagttcta
cgggctctcggagaatgacgagtggacccaggatagggccaaacccgtcacccagatc
gtcagcgccgaggcctggggtagagcagactaa
(SEQ ID NO: 27)

Figure 2a

M Q E V T Q I P A A L S V P E G E N L V L N C S F T D S A I Y N L Q W F R Q
D P G K G L T S L L L I Q S S Q R E Q T S G R L N A S L D K S S G R S T L Y I
A A S Q P G D S A T Y L C A V R P T S G G S Y I P T F G R G T S L I V H P Y I
Q N P D P A V Y Q L R D S K S S D K S V C L F T D F D S Q T N V S Q S K D S
D V Y I T D K C V L D M R S M D F K S N S A V A W S N K S D F A C A N A F
N N S I I P E D T F F P S P E S S Stop
(SEQ ID NO: 28)

P V T Q I V S A E A W G R A D Stop (SEQ ID NO: 29)

Figure 3 pEX746: NY-ESO

```
   1 gttaactacg tcaggtggca cttttcgggg aaatgtgcgc ggaacccta
  51 tttgtttatt tttctaaata cattcaaata tgtatccgct catgagacaa
 101 taaccctgat aaatgcttca ataatattga aaaggaaga gtatgagtat
 151 tcaacatttc cgtgtcgccc ttattccctt ttttgcggca ttttgccttc
 201 ctgttttttgc tcacccagaa acgctggtga agtaaaaga tgctgaagat
 251 cagttgggtg cacgagtggg ttacatcgaa ctggatctca acagcggtaa
 301 gatccttgag agttttcgcc ccgaagaacg ttctccaatg atgagcactt
 351 ttaaagttct gctatgtggc gcggtattat cccgtgttga cgccgggcaa
 401 gagcaactcg gtcgccgcat acactattct cagaatgact tggttgagta
 451 ctcaccagtc acagaaaagc atcttacgga tggcatgaca gtaagagaat
 501 tatgcagtgc tgccataacc atgagtgata acactgcggc caacttactt
 551 ctgacaacga tcggaggacc gaaggagcta accgcttttt tgcacaacat
 601 gggggatcat gtaactcgcc ttgatcgttg gaaccggag ctgaatgaag
 651 ccataccaaa cgacgagcgt gacaccacga tgcctgtagc aatggcaaca
 701 acgttgcgca aactattaac tggcgaacta cttactctag cttcccggca
 751 acaattaata gactggatgg aggcggataa agttgcagga ccacttctgc
 801 gctcggccct tccggctggc tggtttattg ctgataaatc tggagccggt
 851 gagcgtgggt ctcgcggtat cattgcagca ctggggccag atggtaagcc
 901 ctcccgtatc gtagttatct acacgacggg gagtcaggca actatggatg
 951 aacgaaatag acagatcgct gagataggtg cctcactgat taagcattgg
1001 taactgtcag accaagttta ctcatatata ctttagattg atttaccccg
1051 gttgataatc agaaaagccc caaaaacagg aagattgtat aagcaaatat
1101 ttaaattgta acgttaata ttttgttaaa attcgcgtta aattttttgtt
1151 aaatcagctc attttttaac caataggccg aaatcggcaa aatcccttat
1201 aaatcaaaag aatagcccga gatagggttg agtgttgttc cagtttggaa
1251 caagagtcca ctattaaaga acgtggactc caacgtcaaa gggcgaaaaa
1301 ccgtctatca gggcgatggc ccactacgtg aaccatcacc caaatcaagt
1351 tttttggggt cgaggtgccg taaagcacta atcggaacc ctaaagggag
1401 cccccgattt agagcttgac ggggaaagcg aacgtggcga aaaggaagg
1451 gaagaaagcg aaaggagcgg gcgctagggc gctggcaagt gtagcggtca
1501 cgctgcgcgt aaccaccaca cccgccgcgc ttaatgcgcc gctacagggc
1551 gcgtaaaagg atctaggtga agatccttt tgataatctc atgaccaaaa
1601 tccctaacg tgagttttcg ttccactgag cgtcagaccc cgtagaaaag
1651 atcaaaggat cttcttgaga tcctttttt ctgcgcgtaa tctgctgctt
1701 gcaaacaaaa aaaccaccgc taccagcggt ggtttgtttg ccggatcaag
1751 agctaccaac tctttttccg aaggtaactg gcttcagcag agcgcagata
1801 ccaaatactg ttcttctagt gtagccgtag ttaggccacc acttcaagaa
1851 ctctgtagca ccgcctacat acctcgctct gctaatcctg ttaccagtgg
1901 ctgctgccag tggcgataag tcgtgtctta ccgggttgga ctcaagacga
1951 tagttaccgg ataaggcgca gcggtcgggc tgaacggggg gttcgtgcac
2001 acagcccagc ttggagcgaa cgacctacac cgaactgaga tacctacagc
2051 gtgagctatg agaaagcgcc acgcttcccg aagggagaaa ggcggacagg
2101 tatccggtaa gcggcagggt cggaacagga gagcgcacga gggagcttcc
2151 aggggggaaac gcctggtatc tttatagtcc tgtcgggttt cgccaccct
2201 gacttgagcg tcgatttttg tgatgctcgt caggggggcg gagcctatgg
2251 aaaaacgcca gcaacgcggc cttttacgg ttcctggcct tttgctggcc
2301 ttttgctcac atgtaatgtg agttagctca ctcattaggc acccaggct
2351 ttacacttta tgcttccggc tcgtatgttg tgtggaattg tgagcggata
2401 acaatttcac acaggaaaca gctatgacca tgattacgcc aagctacgta
2451 cttaagtatt ctatttcaag gagacagtca taatgaaata cctattgcct
2501 acggcagccg ctggattgtt attactcgcg gcccagccgg ccatggccaa
2551 acaggaggtg acgcagattc ctgcagctct gagtgtccca gaaggagaaa
2601 acttggttct caactgcagt tcactgata gcgctattta caacctccag
2651 tggtttaggc aggaccctgg gaaaggtctc acatctctgt gcttattca
2701 gtcaagtcag agagacaaa caagtcagaa acttaatgcc tcgctggata
2751 aatcatcagg acgtagtact ttatacattg cagcttctca gcctggtgac
2801 tcagccacct acctctgtgc tgtgagccc acatcaggag gaagctacat
2851 acctacattt ggaagaggaa ccagccttat tgttcatccg tatatccaga
2901 acccggatcc tgccgtgtac cagctgagag actctaaatc cagtgacaag
2951 tctgtctgcc tattcaccga ttttgattct caaacaaatg tgtcacaaag
3001 taaggattct gatgtgtata tcacagacaa atgtgtgcta gacatgaggt
3051 ctatggactt caagagcaac agtgctgtgg cctggagcaa caaatctgac
3101 tttgcatgtg caaacgcctt caacaacagc attattccag aagacacctt
3151 cttccccagc ccagaaagtt cctaataacc taggttaatt aagaattctt
3201 taagaagggg atatacatat gaaaaaatta ttattcgcaa ttcctttagt
3251 tgttcctttc tattctcaca gcgcgcaggc tggtgtcact cagacccaa
```

Figure 3 continued

```
3301 aattccaggt cctgaagaca ggacagagca tgacactgca gtgtgcccag
3351 gatatgaacc atgaatacat gtcctggtat cgacaagacc caggcatggg
3401 gctgaggctg attcattact cagttggtgc tggtatcact gaccaaggag
3451 aagtccccaa tggctacaat gtctccagat caaccacaga ggatttcccg
3501 ctcaggctgc tgtcggctgc tccctcccag acatctgtgt acttctgtgc
3551 cagcagttac gtcgggaaca ccggggagct gttttttgga gaaggctcta
3601 ggctgaccgt actggaggac ctgaaaaacg tgttcccacc cgaggtcgct
3651 gtgtttgagc catcagaagc agagatctcc cacacccaaa aggccacact
3701 ggtgtgcctg gccacaggct ctaccccga ccacgtggag ctgagctggt
3751 gggtgaatgg gaaggaggtg cacagtgggg tctgcacaga cccgcagccc
3801 ctcaaggagc agcccgccct caatgactcc agatacgctc tgagcagccg
3851 cctgagggtc tcggccacct tctggcagga cccccgcaac cacttccgct
3901 gtcaagtcca gttctacggg ctctcggaga atgacgagtg gacccaggat
3951 agggccaaac ccgtcaccca gatcgtcagc gccgaggcct ggggtagagc
4001 agacgcggcc gcatctagaa ttcaccatca tcactagact gttgaaagtt
4051 gtttagcaaa acccataca gaaaattcat ttactaacgt ctggaaagac
4101 gacaaaactt tagatcgtta cgctaactat gagggttgtc tgtggaatgc
4151 tacaggcgtt gtagtttgta ctggtgacga aactcagtgt tacggtacat
4201 gggttcctat tgggcttgct atccctgaaa atgagggtgg tggctctgag
4251 ggtggcggtt ctgagggtgg cggttctgag ggtggcggta ctaaacctcc
4301 tgagtacggt gatacaccta ttccgggcta tacttatatc aaccctctcg
4351 acggcactta tccgcctggt actgagcaaa accccgctaa tcctaatcct
4401 tctcttgagg agtctcagcc tcttaatact ttcatgtttc agaataatag
4451 gttccgaaat aggcaggggg cattaactgt ttatacgggc actgttactc
4501 aaggcactga ccccgttaaa acttattacc agtacactcc tgtatcatca
4551 aaagccatgt atgacgctta ctggaacggt aaattcagag actgcgcttt
4601 ccattctggc tttaatgagg atccattcgt ttgtgaatat caaggccaat
4651 cgtctgacct gcctcaacct cctgtcaatg ctggcggcgg ctctggtggt
4701 ggttctggtg gcggctctga gggtggtggc tctgagggtg gcggttctga
4751 gggtggcggc tctgaggag gcggttccgg tggtggctct ggttccggtg
4801 attttgatta tgaaagatg gcaaacgcta ataaggggc tatgaccgaa
4851 aatgccgatg aaaacgcgct acagtctgac gctaaaggca aacttgattc
4901 tgtcgctact gattacggtg ctgctatcga tggtttcatt ggtgacgttt
4951 ccggccttgc taatggtaat ggtgctactg gtgattttgc tggctctaat
5001 tcccaaatgg ctcaagtcgg tgacggtgat aattcacctt taatgaataa
5051 tttccgtcaa tatttacctt ccctccctca atcggttgaa tgtcgccctt
5101 ttgtctttag cgctggtaaa ccatatgaat tttctattga ttgtgacaaa
5151 ataaacttat tccgtggtgt ctttgcgttt cttttatatg ttgccacctt
5201 tatgtatgta tttctacgt ttgctaacat actgcgtaat aaggagtctt
5251 aataaggtac cctctagtca aggcctatag tgagtcgtat tacggactgg
5301 ccgtcgtttt acaacgtcgt gactgggaaa accctggcgt tacccaactt
5351 aatcgccttg cagcacatcc ccctttcgcc agctggcgta atagcgaaga
5401 ggcccgcacc gatcgccctt cccaacagtt gcgcagcctg aatggcgaat
5451 ggcgcttcgc ttggtaataa agcccgcttc ggcgggcttt ttttt
```

(SEQ ID NO: 30)

Figure 4

PEX922-1G4

```
tttttttttgttgcctgctagcgatccaagcaatatccgtatgtctgcgggtatcgcat
tacaatggatgtccccattggggccgttggtgttctcctacgcccagccgttcaaaaa
gtacgatggagacaaggcagaacagttccagtttaacatcggtaaaacctggtaagtg
ttctccgcaaaggaatgtagtggtagtgtagcgatgactttaggcgatcaatataaga
tcgccgggccacgcaaagaactgcaccctccggtgcaaatgggatggtaaggagttta
ttgtgaaaagtggttattagctgcaggtctcggtttagcactggcaacttctgctca
ggcggctgacaaaattgcaatcgtcaacatgggcagcctgttccagcaggtagcgcag
aaaaccggtgtttctaacacgctggaaaatgagttcaaaggccgtgccagcgaactgc
agcgtatggaaaccgatctgcaggctaaaatgaaaaagctgcagtccatgaaagcggg
cagcgatcgcactaagctggaaaagacgtgatggctcagcgccagacttttgctcag
aaagcgcaggcttttgagcaggatcgcgcacgtcgttccaacgaagaacgcggcaaac
tggttactcgtatccagactgctgtgaaatccgttgccaacagccaggatatcgatct
ggttgttgatgcaaacgccgttgcttacaacagcagcgatgtaaaagacatcactgcc
gacgtactgaaacaggttaaataaactagtagtaggaactacgtcaggtggcactttt
cggggaaatgtgcgcggaaccctatttgtttattttttctaaatacattcaaatatgt
atccgctcatgagacaataaccctgataaatgcttcaataatattgaaaaaggaagag
tatgagtattcaacatttccgtgtcgcccttattcccttttttgcggcattttgcctt
cctgttttgctcacccagaaacgctggtgaaagtaaaagatgctgaagatcagttgg
gtgcacgagtgggttacatcgaactggatctcaacagcggtaagatccttgagagttt
tcgccccgaagaacgttctccaatgatgagcacttttaaagttctgctatgtggcgcg
gtattatcccgtgttgacgccgggcaagagcaactcggtcgccgcatacactattctc
agaatgacttggttgagtactcaccagtcacagaaaagcatcttacggatggcatgac
agtaagagaattatgcagtgctgccataaccatgagtgataacactgcggccaactta
cttctgacaacgatcggaggaccgaaggagctaaccgcttttttgcacaacatgggg
atcatgtaactcgccttgatcgttgggaaccggagctgaatgaagccataccaaacga
cgagcgtgacaccacgatgcctgtagcaatggcaacaacgttgcgcaaactattaact
ggcgaactacttactctagcttcccggcaacaattaatagactggatggaggcggata
```

Figure 4 continued aagttgcaggaccacttctgcgctcggcccttccggctggctggtttattgctgataa
atctggagccggtgagcgtgggtctcgcggtatcattgcagcactggggccagatggt
aagccctcccgtatcgtagttatctacacgacggggagtcaggcaactatggatgaac
gaaatagacagatcgctgagataggtgcctcactgattaagcattggtaactgtcaga
ccaagtttactcatatactttagattgatttaccccggttgataatcagaaaagcc
ccaaaaacaggaagattgtataagcaaatatttaaattgtaaacgttaatattttgtt
aaaattcgcgttaaattttttgttaaatcagctcattttttaaccaataggccgaaatc
ggcaaaatcccttataaatcaaaagaatagcccgagatagggttgagtgttgttccag
tttggaacaagagtccactattaaagaacgtggactccaacgtcaaagggcgaaaaac
cgtctatcagggcgatggcccactacgtgaaccatcacccaaatcaagttttttgggg
tcgaggtgccgtaaagcactaaatcggaaccctaaagggagcccccgatttagagctt
gacggggaaagcgaacgtggcgagaaaggaagggaagaaagcgaaaggagcgggcgct
agggcgctggcaagtgtagcggtcacgctgcgcgtaaccaccacacccgccgcgctta
atgcgccgctacagggcgcgtaaaaggatctaggtgaagatccttttttgataatctca
tgaccaaaatcccttaacgtgagttttcgttccactgagcgtcagaccccgtagaaaa
gatcaaaggatcttcttgagatcctttttttctgcgcgtaatctgctgcttgcaaaca
aaaaaccaccgctaccagcggtggtttgtttgccggatcaagagctaccaactcttt
ttccgaaggtaactggcttcagcagagcgcagataccaaatactgttcttctagtgta
gccgtagttaggccaccacttcaagaactctgtagcaccgcctacatacctcgctctg
ctaatcctgttaccagtggctgctgccagtggcgataagtcgtgtcttaccgggttgg
actcaagacgatagttaccggataaggcgcagcggtcgggctgaacggggggttcgtg
cacacagcccagcttggagcgaacgacctacaccgaactgagatacctacagcgtgag
ctatgagaaagcgccacgcttcccgaagggagaaaggcggacaggtatccggtaagcg
gcagggtcggaacaggagagcgcacgagggagcttccaggggaaacgcctggtatct
ttatagtcctgtcgggtttcgccacctctgacttgagcgtcgattttttgtgatgctcg
tcaggggggcggagcctatggaaaaacgccagcaacgcggcctttttacggttcctgg
ccttttgctggccttttgctcacatgtaatgtgagttagctcactcattaggcaccc
aggctttacactttatgcttccggctcgtatgttgtgtggaattgtgagcggataaca
atttcacacaggaaacagctatgaccatgattacgccaagctacgtacttaagtattc

Figure 4 continued

```
tatttcaaggagacagtcataatgaaatacctattgcctacggcagccgctggattgt
tattactcgcggcccagccggccatggccaaacaggaggtgacgcagattcctgcagc
tctgagtgtcccagaaggagaaaacttggttctcaactgcagtttcactgatagcgct
atttacaacctccagtggtttaggcaggaccctgggaaaggtctcacatctctgttgc
ttattcagtcaagtcagagagagcaaacaagtggaagacttaatgcctcgctggataa
atcatcaggacgtagtactttatacattgcagcttctcagcctggtgactcagccacc
tacctctgtgctgtgaggcccacatcaggaggaagctacatacctacatttggaagag
gaaccagccttattgttcatccgtatatccagaacccggatcctgccgtgtaccagct
gagagactctaaatccagtgacaagtctgtctgccattcaccgatttgattctcaa
acaaatgtgtcacaaagtaaggattctgatgtgtatatcacagacaaatgtgtgctag
acatgaggtctatggacttcaagagcaacagtgctgtggcctggagcaacaaatctga
ctttgcatgtgcaaacgccttcaacaacagcattattccagaagacaccttcttcccc
agcccagaaagttcctaataacctaggttaattaagaattctttaagaaggggatata
catatgaaaaaattattattcgcaattcctttagttgttcctttctattctcacagcg
cgcaggctggtgtcactcagaccccaaaattccaggtcctgaagacaggacagagcat
gacactgcagtgtgcccaggatatgaaccatgaatacatgtcctggtatcgacaagac
ccaggcatggggctgaggctgattcattactcagttggtgctggtatcactgaccaag
gagaagtccccaatggctacaatgtctccagatcaaccacagaggatttcccgctcag
gctgctgtcggctgctccctcccagacatctgtgtacttctgtgccagcagttacgtc
gggaacaccggggagctgttttttggagaaggctctaggctgaccgtactggaggacc
tgaaaaacgtgttcccacccgaggtcgctgtgtttgagccatcagaagcagagatctc
ccacacccaaaaggccacactggtgtgcctggccacaggcttctaccccgaccacgtg
gagctgagctggtgggtgaatgggaaggaggtgcacagtggggtctgcacagacccgc
agcccctcaaggagcagcccgccctcaatgactccagatacgctctgagcagccgcct
gagggtctcggccaccttctggcaggaccccgcaaccacttccgctgtcaagtccag
ttctacgggctctcggagaatgacgagtggacccaggatagggccaaacccgtcaccc
agatcgtcagcgccgaggcctggggtagagcagacgcggccgcatctagacatcatca
ccatcatcactagactgttgaaagttgtttagcaaaacccatacagaaaattcattt
actaacgtctggaaagacgacaaaactttagatcgttacgctaactatgagggttgtc
```

Figure 4 continued tgtggaatgctacaggcgttgtagtttgtactggtgacgaaactcagtgttacggtac
atgggttcctattgggcttgctatccctgaaaatgagggtggtggctctgagggtggc
ggttctgagggtggcggttctgagggtggcggtactaaacctcctgagtacggtgata
cacctattccgggctatacttatatcaaccctctcgacggcacttatccgcctggtac
tgagcaaaacccgctaatcctaatccttctcttgaggagtctcagcctcttaatact
ttcatgtttcagaataataggttccgaataggcaggggcattaactgtttatacgg
gcactgttactcaaggcactgaccccgttaaaacttattaccagtacactcctgtatc
atcaaaagccatgtatgacgcttactggaacggtaaattcagagactgcgctttccat
tctggctttaatgaggatccattcgtttgtgaatatcaaggccaatcgtctgacctgc
ctcaacctcctgtcaatgctggcggcggctctggtggtggttctggtggcggctctga
gggtggtggctctgagggtggcggttctgagggtggcggctctgagggaggcggttcc
ggtggtggctctggttccggtgatttgattatgaaaagatggcaaacgctaataagg
gggctatgaccgaaaatgccgatgaaaacgcgctacagtctgacgctaaaggcaaact
tgattctgtcgctactgattacggtgctgctatcgatggtttcattggtgacgtttcc
ggccttgctaatggtaatggtgctactggtgattttgctggctctaattcccaaatgg
ctcaagtcggtgacggtgataattcacctttaatgaataatttccgtcaatatttacc
ttccctccctcaatcggttgaatgtcgcccttttgtctttagcgctggtaaaccatat
gaattttctattgattgtgacaaaataaacttattccgtggtgtctttgcgtttcttt
tatatgttgccacctttatgtatgtattttctacgtttgctaacatactgcgtaataa
ggagtcttaataaggtaccctctagtcaaggcctatagtgagtcgtattacggactgg
ccgtcgttttacaacgtcgtgactgggaaaaccctggcgttacccaacttaatcgcct
tgcagcacatccccctttcgccagctggcgtaatagcgaagaggcccgcaccgatcgc
ccttcccaacagttgcgcagcctgaatggcgaatggcgcttcgcttggtaataaagcc
cgcttcggcgggc (SEQ ID NO: 31)

Figure 5

PEX821

```
gatctcgatcccgcgaaattaatacgactcactatagggagaccacaacggtttccct
ctagaaataattttgtttaactttaagaaggagatatacatatgaacgctggtgtcac
tcagaccccaaaattccaggtcctgaagacaggacagagcatgacactgcagtgtgcc
caggatatgaaccatgaatacatgtcctggtatcgacaagacccaggcatggggctga
ggctgattcattactcagttggtgctggtatcactgaccaaggagaagtccccaatgg
ctacaatgtctccagatcaaccacagaggatttcccgctcaggctgctgtcggctgct
ccctcccagacatctgtgtacttctgtgccagcaggccgggactagcgggagggcgac
cagagcagtacttcgggccgggcaccaggctcacggtcacagaggacctgaaaaacgt
gttcccacccgaggtcgctgtgtttgagccatcagaagcagagatctcccacacccaa
aaggccacactggtgtgcctggccaccggtttctaccccgaccacgtggagctgagct
ggtgggtgaatgggaaggaggtgcacagtggggtctgcacagacccgcagcccctcaa
ggagcagcccgccctcaatgactccagatacgctctgagcagccgcctgagggtctcg
gccaccttctggcaggaccccgcaaccacttccgctgtcaagtccagttctacgggc
tctcggagaatgacgagtggacccaggatagggccaaacccgtcacccagatcgtcag
cgccgaggcctggggtagagcagactaagcttgaattccgatccggctgctaacaaag
cccgaaaggaagctgagttggctgctgccaccgctgagcaataactagcataacccct
tggggcctctaaacgggtcttgaggggttttttgctgaaaggaggaactatatccgga
taattcttgaagacgaaagggcctcgtgatacgcctatttttataggttaatgtcatg
ataataatggtttcttagacgtcaggtggcacttttcggggaaatgtgcgcggaaccc
ctatttgtttatttttctaaatacattcaaatatgtatccgctcatgagacaataacc
ctgataaatgcttcaataatattttgttaaaattcgcgttaaattttgttaaatcag
ctcatttttaaccataggccgaaatcggcaaaatcccttataaatcaaaagaatag
accgagatagggttgagtgttgttccagtttggaacaagagtccactattaaagaacg
tggactccaacgtcaaagggcgaaaaaccgtctatcagggcgatggcccactacgtga
accatcaccctaatcaagttttttggggtcgaggtgccgtaaagcactaaatcggaac
```

Figure 5 continued

```
cctaaagggagcccccgatttagagcttgacggggaaagccggcgaacgtggcgagaa
aggaagggaagaaagcgaaggagcgggcgctagggcgctggcaagtgtagcggtcac
gctgcgcgtaaccaccacacccgccgcgcttaatgcgccgctacagggcgcgtcaggt
ggcacttttcggggaaatgtgcgcggaaccc tatttgtttattttt ctaaatacatt
caaatatgtatccgctcatgagacaataaccctgataaatgcttcaataatattgaaa
aaggaagagtatgagtattcaacatttccgtgtcgcccttattccttttttgcggca
ttttgccttcctgtttttgctcacccagaaacgctggtgaaagtaaaagatgctgaag
atcagttgggtgcacgagtgggttacatcgaactggatctcaacagcggtaagatcct
tgagagttttcgccccgaagaacgttttccaatgatgagcacttttaaagttctgcta
tgtggcgcggtattatcccgtgttgacgccgggcaagagcaactcggtcgccgcatac
actattctcagaatgacttggttgagtactcaccagtcacagaaaagcatcttacgga
tggcatgacagtaagagaattatgcagtgctgccataaccatgagtgataacactgcg
gccaacttacttctgacaacgatcggaggaccgaaggagctaaccgcttttttgcaca
acatgggggatcatgtaactcgccttgatcgttgggaaccggagctgaatgaagccat
accaaacgacgagcgtgacaccacgatgcctgcagcaatggcaacaacgttgcgcaaa
ctattaactggcgaactacttactctagcttcccggcaacaattaatagactggatgg
aggcggataaagttgcaggaccacttctgcgctcggcccttccggctggctggtttat
tgctgataaatctggagccggtgagcgtgggtctcgcggtatcattgcagcactgggg
ccagatggtaagccctcccgtatcgtagttatctacacgacggggagtcaggcaacta
tggatgaacgaaatagacagatcgctgagataggtgcctcactgattaagcattggta
actgtcagaccaagtttactcatatactttagattgatttaaaacttcatttttaa
tttaaaaggatctaggtgaagatcctttttgataatctcatgaccaaaatcccttaac
gtgagttttcgttccactgagcgtcagacccgtagaaaagatcaaaggatcttcttg
agatccttttttt ctgcgcgtaatctgctgcttgcaaacaaaaaaaccaccgctacca
gcggtggtttgtttgccggatcaagagctaccaactcttttccgaaggtaactggct
tcagcagagcgcagataccaaatactgtccttctagtgtagccgtagttaggccacca
cttcaagaactctgtagcaccgcctacatacctcgctctgctaatcctgttaccagtg
gctgctgccagtggcgataagtcgtgtcttaccgggttggactcaagacgatagttac
```

Figure 5 continued cggataaggcgcagcggtcgggctgaacggggggttcgtgcacacagcccagcttgga
gcgaacgacctacaccgaactgagatacctacagcgtgagctatgagaaagcgccacg
cttcccgaagggagaaaggcggacaggtatccggtaagcggcagggtcggaacaggag
agcgcacgagggagcttccaggggaaacgcctggtatctttatagtcctgtcgggtt
tcgccacctctgacttgagcgtcgattttgtgatgctcgtcaggggggcggagccta
tggaaaaacgccagcaacg (SEQ ID NO: 32)

Figure 6 pEX954 gatctcgatcccgcgaaattaatacgactcactatagggagaccacaacggtttccct
ctagaaataattttgtttaactttaagaaggagatataatcgatgtctaactcgagtg
acaagtctgtctgcctattcaccgatttttgattctcaaacaaatgtgtcacaaagtaa
ggattctgatgtgtatatcacagacaaatgtgctagacatgaggtctatggacttc
aagagcaacagtgctgtggcctggagcaacaaatctgactttgcatgtgcaaacgcct
tcaacaacagcattattccagaagacaccttcttccccagcccagaaagttcctaagc
ttgaattccgatccggctgctaacaaagcccgaaaggaagctgagttggctgctgcca
ccgctgagcaataactagcataaccccttggggcctctaaacgggtcttgaggggttt
tttgctgaaaggaggaactatatccggataattcttgaagacgaaagggcctcgtgat
acgcctattttataggttaatgtcatgataataatggtttcttagacgtgaggtggc
acttttcggggaaatgtgcgcggaacccctatttgtttatttttctaaatacattcaa
atatgtatccgctcatgagacaataaccctgataaatgcttcaataatatttgttaa
aattcgcgttaaatttttgttaaatcagctcatttttaaccataggccgaaatcgg
caaaatcccttataaatcaaaagaatagaccgagatagggttgagtgttgttccagtt
tggaacaagagtccactattaaagaacgtggactccaacgtcaaagggcgaaaaaccg
tctatcagggcgatggcccactacgtgaaccatcaccctaatcaagttttttggggtc
gaggtgccgtaaagcactaaatcggaacccaaagggagcccccgatttagagcttga
cggggaaagccggcgaacgtggcgagaaaggaagggaagaaagcgaaggagcgggcg
ctagggcgctggcaagtgtagcggtcacgctgcgcgtaaccaccacacccgccgcgct
taatgcgccgctacagggcgcgtcaggtggcacttttcggggaaatgtgcgcggaacc
cctatttgtttattttctaaatacattcaaatatgtatccgctcatgagacaataac
cctgataaatgcttcaataatattgaaaaggaagagtatgagtattcaacatttccg
tgtcgcccttattcctttttgcggcattttgccttcctgttttgctcacccagaa
acgctggtgaaagtaaaagatgctgaagatcagttgggtgcacgagtgggttacatcg

Figure 6 continued

```
aactggatctcaacagcggtaagatccttgagagttttcgccccgaagaacgttttcc
aatgatgagcacttttaaagttctgctatgtggcgcggtattatcccgtgttgacgcc
gggcaagagcaactcggtcgccgcatacactattctcagaatgacttggttgagtact
caccagtcacagaaaagcatcttacggatggcatgacagtaagagaattatgcagtgc
tgccataaccatgagtgataacactgcggccaacttacttctgacaacgatcggagga
ccgaaggagctaaccgcttttttgcacaacatggggatcatgtaactcgccttgatc
gttgggaaccggagctgaatgaagccataccaaacgacgagcgtgacaccacgatgcc
tgcagcaatggcaacaacgttgcgcaaactattaactggcgaactacttactctagct
tcccggcaacaattaatagactggatggaggcggataaagttgcaggaccacttctgc
gctcggcccttccggctggctggtttattgctgataaatctggagccggtgagcgtgg
gtctcgcggtatcattgcagcactggggccagatggtaagccctcccgtatcgtagtt
atctacacgacggggagtcaggcaactatggatgaacgaaatagacagatcgctgaga
taggtgcctcactgattaagcattggtaactgtcagaccaagtttactcatatatact
ttagattgatttaaaacttcattttaatttaaaaggatctaggtgaagatcctttt
gataatctcatgaccaaaatcccttaacgtgagttttcgttccactgagcgtcagacc
ccgtagaaaagatcaaaggatcttcttgagatcctttttttctgcgcgtaatctgctg
cttgcaaacaaaaaaaccaccgctaccagcggtggtttgtttgccggatcaagagcta
ccaactcttttttccgaaggtaactggcttcagcagagcgcagataccaaatactgtcc
ttctagtgtagccgtagttaggccaccacttcaagaactctgtagcaccgcctacata
cctcgctctgctaatcctgttaccagtggctgctgccagtggcgataagtcgtgtctt
accgggttggactcaagacgatagttaccggataaggcgcagcggtcgggctgaacgg
ggggttcgtgcacacagcccagcttggagcgaacgacctacaccgaactgagatacct
acagcgtgagctatgagaaagcgccacgcttcccgaagggagaaaggcggacaggtat
ccggtaagcggcagggtcggaacaggagagcgcacgagggagcttccaggggaaacg
cctggtatctttatagtcctgtcgggtttcgccacctctgacttgagcgtcgattttt
gtgatgctcgtcaggggggcggagcctatggaaaaacgccagcaacgcggccttttta
cggttcctggccttttgctggccttttgctcacatgttctttcctgcgttatccctg
attctgtggataaccgtattaccgcctttgagtgagctgataccgctcgccgcagccg
aacgaccgagcgcagcgagtcagtgagcgaggaagcggaagagcgcctgatgcggtat
```

Figure 6 continued

```
tttctccttacgcatctgtgcggtatttcacaccgcaatggtgcactctcagtacaat
ctgctctgatgccgcatagttaagccagtatacactccgctatcgctacgtgactggg
tcatggctgcgccccgacacccgccaacacccgctgacgcgccctgacgggcttgtct
gctcccggcatccgcttacagacaagctgtgaccgtctccgggagctgcatgtgtcag
aggttttcaccgtcatcaccgaaacgcgcgaggcag
```

(SEQ ID NO: 33)

Figure 7a ggaatacaagtggagcagagtcctccagacctgattctccaggagggagccaattccacgctgcggtgcaatttttctgact
ctgtgaacaatttgcagtggtttcatcaaaacccttggggacagctcatcaacctgttttacattccctcagggacaaaacaga
atggaagattaagcgccacgactgtcgctacggaacgctacagcttattgtacatttcctcttcccagaccacagactcaggc
gtttatttctgtgctgtggactctgctacctcaggaacctacaaatacatctttggaacaggcaccaggctgaaggttttagcaa
atatccagaaccctgaccctgccgtgtaccagctgagagactctaaatccagtgacaagtctgtctgcctattcaccgattttg
attctcaaacaaatgtgtcacaaagtaaggattctgatgtgtatatcacagacaaatgtgtgctagacatgaggtctatggactt
caagagcaacagtgctgtggcctggagcaacaaatctgactttgcatgtgcaaacgccttcaacaacagcattattccagaa
gacaccttcttccccagcccagaaagttcctaa
(SEQ ID No: 35)

Figure 7b aacgctggtgtcactcagaccccaaaattccaggtcctgaagacaggacagagcatgacactgcagtgtgcccaggatatg
aaccatgaatacatgtcctggtatcgacaagacccaggcatggggctgaggctgattcattactcagttggtgctggtatcac
tgaccaaggagaagtccccaatggctacaatgtctccagatcaaccacagaggatttcccgctcaggctgctgtcggctgct
ccctcccagacatctgtgtacttctgtgccagcagttaccaaggcactgaagctttctttggacaaggcaccagactcacagtt
gtagaggacctgaaaaacgtgttcccacccgaggtcgctgtgtttgagccatcagaagcagagatctcccacacccaaaag
gccacactggtgtgcctggccacaggcttctaccccgaccacgtggagctgagctggtgggtgaatgggaaggaggtgc
acagtggggtctgcacagacccgcagcccctcaaggagcagcccgccctcaatgactccagatacgctctgagcagccg
cctgagggtctcggccaccttctggcaggaccccgcaaccacttccgctgtcaagtccagttctacgggctctcggagaat
gacgagtggacccaggatagggccaaacccgtcacccagatcgtcagcgccgaggcctggggtagagcagactaa
(SEQ ID No: 36)

Figure 8a

G I Q V E Q S P P D L I L Q E G A N S T L R C N F S D S V
N N L Q W F H Q N P W G Q L I N L F Y I P S G T K Q N G R
L S A T T V A T E R Y S L L Y I S S S Q T T D S G V Y F C
A V D S A T S G T Y K Y I F G T G T R L K V L A I Q N P D
P A V Y Q L R D S K S S D K S V C L F T D F D S Q T N V S
Q S K D S D V Y I T D K C V L D M R S M D F K S N S A V A
W S N K S D F A C A N A F N N S I I P E D T F F P S P E S
S (SEQ ID No: 38)

Figure 8b

N A G V T Q T P K F Q V L K T G Q S M T L Q C A Q D M N H
E Y M S W Y R Q D P G M G L R L I H Y S V G A G I T D Q G
E V P N G Y N V S R S T T E D F P L R L L S A A P S Q T S
V Y F C A S S Y Q G T E A F F G Q G T R L T V V E D L K N
V F P P E V A V F E P S E A E I S H T Q K A T L V C L A T
G F Y P D H V E L S W W V N G K E V H S G V C T D P Q P L
K E Q P A L N D S R Y A L S S R L R V S A T F W Q D P R N
H F R C Q V Q F Y G L S E N D E W T Q D R A K P V T Q I V
S A E A W G R A D (SEQ ID No: 39)

Figure 9a ccatcgatggcccagaaggaggtggagcagaattctggaccccctcagtgttccagagggagccattgcctctctcaattgc
acttacagtgaccgaggttcccagtccttcttctggtacagacaatattctgggaaaagccctgagttgataatgttcatatactc
caatggtgacaaagaagatggaaggtttacagcacagctcaataaagccagccagtatatttccctgctcatcagagactcc
aagctcagtgattcagccacctacctctgtgcggtgcgcacaaattccgggtatgcactcaacttcggcaaaggcacctcgc
tgttggtcacaccccatatccagaaccctgaccctgccgtgtaccagctgagagactctaagtcgagtgacaagtctgtctgc
ctattcaccgattttgattctcaaacaaatgtgtcacaaagtaaggattctgatgtgtatatcacagacaaatgtgtgctagacat
gaggtctatggacttcaagagcaacagtgctgtggcctggagcaacaaatctgactttgcatgtgcaaacgccttcaacaac
agcattattccagaagacaccttcttccccagcccagaaagttcctaa
(SEQ ID No: 54)

Figure 9b tctctcattaatggaggctggagtcacacaaagtcccacacacctgatcaaaacgagaggacagcaagtgactctgagatg
ctctcctaagtctgggcatgacactgtgtcctggtaccaacaggccctgggtcaggggccccagtttatctttcagtattatga
ggaggaagagagacagagaggcaacttccctgatcgattctcaggtcaccagttccctaactatagctctgagctgaatgtg
aacgccttgttgctgggggactcggccctctatctctgtgccagcagcgacaccgtctcctacgagcagtacttcgggccgg
gcaccaggctcacggtcacagaggacctgaaaaacgtgttccacccgaggtcgctgtgtttgagccatcagaagcagag
atctcccacacccaaaaggccacactggtgtgcctggccaccggtttctaccccgaccacgtggagctgagctggtgggtg
aatgggaaggaggtgcacagtgggtctgcacagacccgcagcccctcaaggagcagcccgccctcaatgactccagat
acgctctgagcagccgcctgagggtctcggccaccttctggcaggaccccgcaaccacttccgctgtcaagtccagttct
acgggctctcggagaatgacgagtggacccaggatagggccaaacccgtcacccagatcgtcagcgccgaggcctggg
gtagagcagactaa
(SEQ ID No: 55)

Figure 10a

M A Q K E V E Q N S G P L S V P E G A I A S L N C T Y S D R G S Q S F
F W Y R Q Y S G K S P E L I M F I Y S N G D K E D G R F T A Q L N K A
S Q Y I S L L I R D S K L S D S A T Y L C A V R T N S G Y A L N F G K
G T S L L V T P H I Q N P D P A V Y Q L R D S K S S D K S V C L F T D
F D S Q T N V S Q S K D S D V Y I T D K C V L D M R S M D F K S N S A
V A W S N K S D F A C A N A F N N S I I P E D T F F P S P E S S (SEQ ID No: 56)

Figure 10b

M E A G V T Q S P T H L I K T R G Q Q V T L R C S P K S G H D T V S W
Y Q Q A L G Q G P Q F I F Q Y Y E E E E R Q R G N F P D R F S G H Q F
P N Y S S E L N V N A L L L G D S A L Y L C A S S D T V S Y E Q Y F G
P G T R L T V T E D L K N V F P P E V A V F E P S E A E I S H T Q K A
T L V C L A T G F Y P D H V E L S W W V N G K E V H S G V C T D P Q P
L K E Q P A L N D S R Y A L S S R L R V S A T F W Q D P R N H F R C Q
V Q F Y G L S E N D E W T Q D R A K P V T Q I V S A E A W G R A D (SEQ ID No: 57)

METHOD OF IMPROVING T CELL RECEPTORS

This application is a continuation of Ser. No. 11/579,874 filed Nov. 8, 2006 as a national stage application of co-pending PCT application PCT/GB2005/001781 filed May 10, 2005, which claims the benefit of GB 0411125.8 filed May 19, 2004 and GB 0419646.5 filed Sep. 3, 2004. Each of these applications is incorporated herein by reference in its entirety.

This application incorporates by reference the contents of a 50.5 KB text file created Oct. 7, 2008 and named "53MG_sequence_listing.txt," which is the sequence listing for this application.

The invention relates to a method of increasing the affinity and/or decreasing the off-rate of a given T cell receptor ("TCR") specific for a given target peptide-MHC complex ("pMHC"), comprising creating a plurality of TCRs having an α chain CDR2 (Complementarity Determining Region-2) sequence and/or a β chain CDR2 sequence different from the corresponding CDR2 sequence(s) of the given TCR, determining the affinity and/or off-rate of members of said plurality of TCRs for the target pMHC, and selecting one or more members having at least a 10-fold greater affinity for the target pMHC than the given TCR and/or a 10-fold slower off-rate for the target pMHC than the given TCR.

BACKGROUND TO THE INVENTION

TCRs mediate the recognition of specific pMHC by T cells and, as such, are essential to the functioning of the cellular arm of the immune system. The native TCR is a heterodimeric cell surface protein of the immunoglobulin superfamily which is associated with invariant proteins of the CD3 complex involved in mediating signal transduction. TCRs exist in αβ and γδ forms, which are structurally similar but have quite distinct anatomical locations and probably functions. The MHC class I and class II ligands are also immunoglobulin superfamily proteins but are specialised for antigen presentation, with a highly polymorphic peptide binding site which enables them to present a diverse array of short peptide fragments at the antigen presenting cell ("APC") surface.

Two further classes of proteins are known to be capable of functioning as TCR ligands, (1) CD1 antigens are MHC class I-related molecules whose genes are located on a different chromosome from the classical MHC class I and class II antigens. CD1 molecules are capable of presenting peptide and non-peptide (eg lipid, glycolipid) moieties to T cells in a manner analogous to conventional class I and class II-MHC-peptide complexes. See, for example (Barclay et al, (1997) The Leucocyte Antigen Factsbook $2^{nd}$ Edition, Academic Press) and (Bauer (1997) Eur J Immunol 27 (6) 1366-1373)). Bacterial superantigens are soluble toxins which are capable of binding both class II MHC molecules and a subset of TCRs. (Fraser (1989) Nature 339 221-223). Many superantigens exhibit specificity for one or two Vbeta segments, whereas others exhibit more promiscuous binding. In any event, superantigens are capable of eliciting an enhanced immune response by virtue of their ability to stimulate subsets of T cells in a polyclonal fashion.

The extracellular portion of native heterodimeric αβ and γδ TCRs consist of two polypeptides each of which has a membrane-proximal constant domain, and a membrane-distal variable domain. Each of the constant and variable domain includes an intra-chain disulfide bond. The variable domains contain the highly polymorphic loops analogous to the complementarity determining regions (CDRs) of antibodies. CDR3 of αβ TCRs predominantly interact with the peptide presented by MHC, and CDRs 1 and 2 of αβ TCRs predominantly interact with the peptide and the MHC. The diversity of TCR variable domain sequences is generated via somatic rearrangement of linked variable (V), diversity (D), joining (J), and constant genes Functional α and γ chain TCR polypeptides are formed by rearranged V-J-C regions, whereas β and δ chains consist of V-D-J-C regions. The extracellular constant domain has a membrane proximal region and an immunoglobulin region. There are single α and δ chain constant domains, known as TRAC and TRDC respectively and the β chain constant domain is composed of one of two different β constant domains, known as TRBC1 and TRBC2 (IMGT nomenclature). There are four amino acid changes between these β constant domains, three of which are within the domains used to produce the single-chain TCRs displayed on phage particles of the present invention. These changes are all within exon 1 of TRBC1 and TRBC2: $N4K_5$->$K_4N_5$ and $F_{37}$->Y (IMGT numbering, differences TRBC1->TRBC2), the final amino acid change between the two TCR β chain constant regions being in exon 3 of TRBC1 and TRBC2: $V_1$->E. The constant γ domain is composed of one of either TRGC1, TRGC2 (2×) or TRGC2 (3×). The two TRGC2 constant domains differ only in the number of copies of the amino acids encoded by exon 2 of this gene that are present.

The extent of each of the TCR extracellular domains is somewhat variable. However, a person skilled in the art can readily determine the position of the domain boundaries using a reference such as The T Cell Receptor Facts Book, Lefranc & Lefranc, Publ. Academic Press 2001.

TCRs can be prepared by recombinant means. A number of constructs have been devised to date for the production of recombinant TCRs. These constructs fall into two broad classes, single-chain TCRs ("scTCRs") and dimeric TCRs ("dTCRs").

Display Methods

Particle display methods have primarily been used to identify proteins with desirable properties such as enhanced expression yields, binding and/or stability characteristics. These methods involve creating a diverse pool or 'library' of proteins or polypeptides expressed on the surface of nucleoprotein particles. These particles have two key features, firstly each particle presents a single variant protein or polypeptide, and secondly the genetic material encoding the expressed protein or polypeptide is associated with that of the particle. This library is then subjected to one or more rounds of selection. For example, this may consist of contacting a ligand with a particle-display library of mutated receptors and identifying which mutated receptors bind the ligand with the highest affinity. Once the selection process has been completed the receptor or receptors with the desired properties can be isolated, and their genetic material can be amplified in order to allow the receptors to be sequenced.

Particularly preferred is the phage display technique which is based on the ability of bacteriophage particles to express a heterologous peptide or polypeptide fused to their surface proteins. (Smith (1985) Science 217 1315-1317). The procedure is quite general, and well understood in the art for the display of polypeptide monomers. However, in the case of polypeptides that in their native form associate as dimers, only the phage display of antibodies appears to have been thoroughly investigated.

For monomeric polypeptide display there are two main procedures:

Firstly (Method A) by inserting into a vector (phagemid) DNA encoding the heterologous peptide or polypeptide fused to the DNA encoding a bacteriophage coat protein. The expression of phage particles displaying the heterologous peptide or polypeptide is then carried out by transfecting bacterial cells with the phagemid, and then infecting the transformed cells with a 'helper phage'. The helper phage acts as a source of the phage proteins not encoded by the phagemid required to produce a functional phage particle.

Secondly (Method B), by inserting DNA encoding the heterologous peptide or polypeptide into a complete phage genome fused to the DNA encoding a bacteriophage coat protein. The expression of phage particles displaying the heterologous peptide or polypeptide is then carried out by infecting bacterial cells with the phage genome. This method has the advantage of the first method of being a 'single-step' process. However, the size of the heterologous DNA sequence that can be successfully packaged into the resulting phage particles is reduced. M13, T7 and Lambda are examples of suitable phages for this method.

A variation on (Method B) the involves adding a DNA sequence encoding a nucleotide binding domain to the DNA in the phage genome encoding the heterologous peptide be displayed, and further adding the corresponding nucleotide binding site to the phage genome. This causes the heterologous peptide to become directly attached to the phage genome. This peptide/genome complex is then packaged into a phage particle which displays the heterologous peptide. This method is described in WO 99/11785.

The phage particles can then be recovered and used to study the binding characteristics of the heterologous peptide or polypeptide. Once isolated, phagemid or phage DNA can be recovered from the peptide- or polypeptide-displaying phage particle, and this DNA can be replicated via PCR. The PCR product can be used to sequence the heterologous peptide or polypeptide displayed by a given phage particle.

The phage display of single-chain antibodies and fragments thereof, has become a routine means of studying the binding characteristics of these polypeptides. There are numerous books available that review phage display techniques and the biology of the bacteriophage. (See, for example, Phage Display—A Laboratory Manual, Barbas et al., (2001) Cold Spring Harbour Laboratory Press).

A third phage display method (Method C) relies on the fact that heterologous polypeptides having a cysteine residue at a desired location can be expressed in a soluble form by a phagemid or phage genome, and caused to associate with a modified phage surface protein also having a cysteine residue at a surface exposed position, via the formation of a disulphide linkage between the two cysteines. WO 01/05950 details the use of this alternative linkage method for the expression of single-chain antibody-derived peptides.

High Affinity TCRs

T cells mature in the thymus where they undergo at least two selection mechanisms, generally referred to as positive and negative selection. The structures of most, or all, TCRs are believed to share certain general architectural features (Chothia, et al, *Embo J* (1988) 7: 3745-55) that provide a framework suitable for MHC/peptide binding by the variable complementarity determining regions (CDRs). Thus, most TCRs may have intrinsic affinity for MHC/peptide complexes (Chothia, et al, *Embo J* (1988) 7: 3745-55). In the thymus, only TCRs with a certain minimal level of affinity for one of the MHC molecules to which they are presented (the "self" MHC molecules) will be positively selected. T cells with high affinity for one of the self MHC molecules will be negatively selected (Amsen & Kruisbeek. (1998). *Immunol Rev* 165: 209-29. Sebzda, et al (1999). *Annu Rev Immunol* 17: 829-74).

TCRs in the cellular immunity can be considered to be analogous to antibodies in the humoral immunity. Antibodies have been successfully used, either as therapeutic agents in their own right (e.g. Herceptin) or as targeting agents (e.g. mylotarg), and interest in this area continues to grow. Similar strategies could be devised using T cell receptors. Thus, soluble TCRs are useful, not only for the purpose of investigating specific TCR-pMHC interactions, but also as a diagnostic tool to detect infection, or to detect autoimmune disease markers, or to detect the efficacy of T cell vaccines. Soluble TCRs also have applications in staining, for example to stain cells for the presence of a particular viral antigen presented in the context of the MHC. Similarly, soluble TCRs can be used to deliver a therapeutic agent, for example a cytotoxic compound or an immunostimulating compound, to cells presenting a particular antigen.

However, two factors have hindered the exploitation of TCRs in this way. Firstly, a generally applicable method for the production of soluble (i.e. non-membrane bound) T cell receptors has not been available until recently. Secondly, the affinity of the T cell receptor for its specific pMHC ligand is much lower ($K_D$ in the μM range) than for antibodies ($K_D$ in the nM range). This lower affinity of the TCR is thought to be a result of negative selection during development, and it is therefore probably not possible to find TCRs with high affinity for self-MHC-peptide complexes (Salzmann & Bachmann, *Molecular Immunology,* 1998, 35:65-71

BRIEF DESCRIPTION OF THE INVENTION

The present invention is based on the finding that the introduction of mutations into the TCR α chain CDR2 sequence and/or TCR β chain CDR2 sequence of a TCR which binds to a given peptide-MHC can result in at least a 10-fold greater affinity and/or 10 fold slower off-rate for the interaction with said pMHC. Since each of the α and β chains contains three CDR sequences (CDR1, CDR2 and CDR3) it was unexpected that the mutation of only the CDR2 sequence could give rise to TCRs with such improvements in affinity and/or off-rate. It is particularly unexpected, since it is the CDR3 region which is considered predominant in the interaction with the peptide of the pMHC, and therefore it is mutation of the CDR3 sequence which might be expected to be the most promising strategy for increasing affinity and/or decreasing off-rate.

DETAILED DESCRIPTION OF THE INVENTION

In one broad aspect the invention provides a method of increasing the affinity and/or decreasing the off-rate of a given TCR specific for a given target pMHC, comprising creating a plurality of TCRs having an α chain CDR2 sequence and/or a β chain CDR2 sequence different from the corresponding CDR2 sequence(s) of the given TCR, determining the affinity and/or off-rate of members of said plurality of TCRs for the target pMHC, and selecting one or more members having at least a 10-fold greater affinity for the target pMHC than the given TCR and/or a 10-fold slower off-rate for the target pMHC than the given TCR.

One embodiment of the method of the invention comprises (a) creating a first plurality of TCRs which, relative to the given TCR, are mutated in the α chain CDR2 sequence but not the β chain CDR2 sequence, (b) separately creating a second plurality of TCRs which, relative to the given TCR, are mutated in the β chain CDR2 sequence but not the α chain CDR2 sequence, (c) determining the affinity and/or off-rate of members of said first and second pluralities of TCRs for the target pMHC, and selecting one or more members of each plurality having at least a 10-fold greater affinity for the target pMHC than the given TCR and/or a 10-fold slower off-rate for the target pMHC than the given TCR, (d) determining the CDR2 sequences of the selected members of each plurality, and (e) creating one or more TCRs each having an α chain CDR2 sequence of the first plurality and a β chain CDR2 sequence of the second plurality, and (f) determining the affinity and/or off-rate of the TCR or TCRs created in step (e) for the target pMHC, and selecting one or more thereof having at least a 10-fold greater affinity for the target pMHC than the given TCR and/or a 10-fold slower off-rate for the target pMHC than the given TCR.

Another embodiment of the method of the invention comprises (a) providing nucleic acid coding for both the α and β chains of the given TCR, (b) subjecting said nucleic acid to mutagenesis of one or more codons of the α chain CDR2 sequence and one or more codons of the β chain CDR2 sequence, (c) from the mutated nucleic acid of step (b) creating a plurality of TCRs which, relative to the given TCR, are mutated in one or more amino acids of the α chain CDR2 sequence and one or more amino acids of the β chain CDR2 sequence, and (d) determining the affinity and/or off-rate of members of said plurality of TCRs for the target pMHC, and selecting one or more members having at least a 10-fold greater affinity for the target pMHC than the given TCR and/or a 10-fold slower off-rate for the target pMHC than the given TCR.

In step (b) of the foregoing embodiment, the said nucleic acid may be subjected to mutagenesis of up to three consecutive codons of the α chain CDR2 sequence and up to three consecutive codons of the β chain CDR2 sequence, and in step (c) a plurality of TCRs may be greated created which, relative to the given TCR, are mutated in up to 3 consecutive amino acids of the α chain CDR2 sequence and up to three consecutive amino acids of the β chain CDR2 sequence.

In a preferred embodiment of the inventions one or more members of the plurality of TCRs having at least a 50-fold greater affinity and/or 50-fold slower off-rate for the target pMHC than the given TCR is/are selected.

In another preferred embodiment of the inventions one or more members of the plurality of TCRs having at least a 100-fold greater affinity and/or 100-fold slower off-rate for the target pMHC than the given TCR is/are selected.

In a further preferred embodiment of the inventions one or more members of the plurality of TCRs having at least a 500-fold greater affinity and/or 500-fold slower off-rate for the target pMHC than the given TCR is/are selected.

One embodiment the method of the invention includes the additional steps of determining the CDR2 sequence(s) of a TCR thereby selected, and preparing a stock of TCRs incorporating the thus-determined CDR2 sequence.

In the context of the present invention the term "TCRs having at least an x-fold greater affinity and/or a x-fold slower off-rate for the target pMHC than the given TCR" is understood to mean that when measured by a known method one or both of the said improvements in the kinetics of the interaction has/have been made.

For example when x=10, if the $K_D$ of the given TCR for the target pMHC is 10 μM all selected TCRs comprising a mutated TCR α chain CDR2 sequence and/or TCR β chain CDR2 sequence having a $K_D$ for the target pMHC of less than or equal to 1 μM will fit this criterion; and when x=10, if the $k_{off}$ of the given TCR for the target pMHC is $1 \times 10^{-3}$ $S^{-1}$ all selected TCRs comprising a mutated TCR α chain CDR2 sequence and/or TCR β chain CDR2 sequence having a $k_{off}$ for the target pMHC of less than or equal to $1 \times 10^{-4}$ $S^{-1}$ will fit this criterion.

A suitable method for determining the affinity and/or off-rate for the target pMHC is/are determined by Surface Plasmon Resonance. Example 6 herein provides a detailed description of how such measurements are carried out.

Production of a Plurality of TCRs Comprising CDR2 Mutations

There are a number of methods of creating a plurality of mutated TCRs.

These methods fall into two categories:

(i) The production of a plurality of mutated TCRs associated with nucleoproteins to form a TCR library, in which there is a linkage between individual TCR mutants and the genetic material by which they are encoded, such nucleoprotein-associated TCR libraries are particularly suited for use in panning methods that provide information on the ability of the members of the library to bind to a particular TCR ligand, such as a pMHC, in parallel. Several members of the TCR library selected by this panning step may then undergo further affinity and/or off-rate assessment in series.

(ii) The production of soluble mutant TCRs lacking any associated nucleoprotein. Such soluble TCRs are not suited for the preparation of TCR libraries, and each member of a plurality of these soluble TCRs would generally require individual affinity and/or off-rate assessment.

As used herein the term "soluble TCR" is understood to refer to any TCR that:
  (i) lacks the native transmembrane domain thereof and
  (ii) is not associated with a nucleoprotein and
  (iii) retains the ability to bind to its cognate pMHC.

As is known to those skilled in the art the location of the CDR2 sequence within a specific human TCR α chain or human TCR β chain amino acid sequence can be located by numbering the variable domain residues using the IMGT numbering system. (The T Cell Factsbook $2^{nd}$ Edition, Lefranc and LeFranc Academic Press 2001) Using this system the CDR2 sequence of both TCR α chains and β chains consist of all the amino acids present between residue numbers 56-65 inclusive of the variable domain.

As will be obvious to those skilled in the art the mutation(s) introduced into the TCR α chain CDR2 sequence and/or TCR β chain CDR2 sequence may be one or more of substitution(s), deletion(s) or insertion(s). These CDR2 mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding PCR mutagenesis and restriction enzyme-based cloning see (Sambrook & Russell, (2001) Molecular Cloning—A Laboratory Manual ($3^{rd}$ Ed.) CSHL Press) Further information on LIC procedures can be found in (Rashtchian, (1995) *Curr Opin Biotechnol* 6 (1): 30-6)

Further embodiments are provided by TCRs for use in the present invention in which 2 or more amino acids in the TCR α chain CDR2 and/or TCR β CDR2 chain sequence is/are mutated.

As is known to those skilled in the art single-point or multiple mutations could be introduced into the one or both CDR2 sequences of individual soluble TCRs by site-directed mutagenesis to produce a plurality of mutant TCRs for affinity and/or off-rate assessment.

However, this is a relatively time-consuming method not ideally suited to the production and testing of a large number of TCR mutants. Therefore, library-based approaches are preferred for the creation of a plurality of TCRs comprising a mutated α chain CDR2 sequence and/or a β chain CDR2 sequence. The Examples herein provide a detailed description of the methods required to produce such a library Methods of Isolating High Affinity TCRs Comprising CDR2 Mutations In one embodiment of the invention said plurality of TCRs are created in soluble form and are contacted in series with the target pMHC for the purpose of determining the affinities and/or off-rates of those which bind thereto and selecting those which have the desired affinities and/or off-rates.

In a preferred embodiment of the invention a plurality of TCRs is created as a diverse library of phage-displayed αβ dimeric TCRs, wherein diversity resides in said CDR2 sequences.

In an alternative embodiment of the invention said plurality of TCRs is created as a diverse library of ribosome-displayed αβ single chain TCRs, wherein diversity resides at least in said CDR2 sequences. WO 2004/044004 provides a description of the methods required to display single-chain TCRs (scTCRs) on ribosomes.

The Displayed TCRs

The following are the preferred TCR designs for the display of TCRs comprising CDR2 mutations by association with nucleoproteins. It should be noted that these TCR designs are equally suited for use as soluble TCRs absent the associated nucleoprotein.

Displayed dTCRs

In one preferred embodiment of the invention, displayed αβ dimeric TCRs comprise a first polypeptide wherein a sequence corresponding to a TCR α chain variable domain sequence is fused to the N terminus of a sequence corresponding to a TCR α chain constant domain extracellular sequence, and a second polypeptide wherein a sequence corresponding to a TCR β chain variable domain sequence fused to the N terminus a sequence corresponding to a TCR β chain constant domain extracellular sequence, the first and second polypeptides being linked by a disulfide bond which has no equivalent in native αβ T cell receptors, and wherein one of said first or second polypeptides is linked by a peptide bond at its C-terminus to a surface exposed amino acid residue of the nucleoprotein, usually a phage particle.

In a specific embodiment of the invention the first and second TCR polypeptides are linked by a disulfide bond between cysteine residues substituted for Thr 48 of exon 1 of TRAC*01 and Ser 57 of exon 1 of TRBC1*01 or TRBC2*01 or the non-human equivalent thereof, and one of said first or second polypeptides are linked by a peptide bond at its C-terminus to a surface exposed amino acid residue of the phage particle.

The residues for mutation to cysteine in order to form the non-native disulfide interchain bind are identified using ImMunoGeneTics (IMGT) nomenclature. (The T cell Receptor Factsbook 2$^{nd}$ Edition (2001) LeFranc and Lefranc, Academic Press) WO 03/020763 provides a detailed description of the methods required to introduce the specified non-native disulfide interchain bond and alternative residues between which it may be sited.

Displayed scTCR

In another embodiment of the invention displayed αβ scTCR polypeptides may, for example, comprise a first segment constituted by an amino acid sequence corresponding to a TCR α variable domain sequence fused to the N terminus of an amino acid sequence corresponding to a TCR α chain constant domain extracellular sequence, a second segment constituted by an amino acid sequence corresponding to a TCR β chain variable domain fused to the N terminus of an amino acid sequence corresponding to TCR β chain constant domain extracellular sequence, a linker sequence linking the C terminus of the first segment to the N terminus of the second segment, or vice versa, and a disulfide bond between the first and second chains, said disulfide bond being one which has no equivalent in native αβ T cell receptors, the length of the linker sequence and the position of the disulfide bond being such that the variable domain sequences of the first and second segments are mutually orientated substantially as in native αβ T cell receptors.

Alternatively, the displayed scTCR may be one which has a first segment constituted by an amino acid sequence corresponding to a TCR α chain variable domain a second segment constituted by an amino acid sequence corresponding to a TCR β chain variable domain sequence fused to the N terminus of an amino acid sequence corresponding to a TCR β chain constant domain extracellular sequence, and a linker sequence linking the C terminus of the first segment to the N terminus of the second segment, or one which has a first segment constituted by an amino acid sequence corresponding to a TCR β chain variable domain a second segment constituted by an amino acid sequence corresponding to a TCR α chain variable domain sequence fused to the N terminus of an amino acid sequence corresponding to a TCR α chain constant domain extracellular sequence, and a linker sequence linking the C terminus of the first segment to the N terminus of the second segment dTCR Polypeptide Pair and scTCR Polypeptide The constant domain extracellular sequences present in the displayed scTCRs or dTCRs preferably correspond to those of a human TCR, as do the variable domain sequences. However, the correspondence between such sequences need not be 1:1 on an amino acid level. N- or C-truncation, and/or amino acid deletion and/or substitution relative to the corresponding human TCR sequences is acceptable. In particular, because the constant domain extracellular sequences present in the first and second segments are not directly involved in contacts with the ligand to which the scTCR or dTCR binds, they may be shorter than, or may contain substitutions or deletions relative to, extracellular constant domain sequences of native TCRs.

The constant domain extracellular sequence present in one of the displayed dTCR polypeptide pair, or in the first segment of a displayed scTCR polypeptide may include a sequence corresponding to the extracellular constant Ig domain of a TCR α chain, and/or the constant domain extracellular sequence present in the other member of the pair or second segment may include a sequence corresponding to the extracellular constant Ig domain of a TCR β chain.

In one embodiment of the invention, one member of the displayed dTCR polypeptide pair, or the first segment of the displayed scTCR polypeptide, corresponds to substantially all the variable domain of a TCR α chain fused to the N terminus of substantially all the extracellular domain of the constant domain of an TCR α chain; and/or the other member of the pair or second segment corresponds to substantially all the variable domain of a TCR β chain fused to the N terminus of substantially all the extracellular domain of the constant domain of a TCR β chain.

In another embodiment, the constant domain extracellular sequences present in the displayed dTCR polypeptide pair, or first and second segments of the displayed scTCR polypeptide, correspond to the constant domains of the α and β chains of a native TCR truncated at their C termini such that the cysteine residues which form the native inter-chain disulfide bond of the TCR are excluded. Alternatively those cysteine residues may be substituted by another amino acid residue such as serine or alanine, so that the native disulfide bond is deleted. In addition, the native TCR β chain contains an unpaired cysteine residue and that residue may be deleted from, or replaced by a non-cysteine residue in, the β sequence of the scTCR of the invention.

In one particular embodiment of the invention, the TCR α and β chain variable domain sequences present in the displayed dTCR polypeptide pair, or first and second segments of the displayed scTCR polypeptide, may together correspond to the functional variable domain of a first TCR, and the TCR α and β chain constant domain extracellular sequences present in the dTCR polypeptide pair or first and second segments of the scTCR polypeptide may correspond to those of a second TCR, the first and second TCRs being from the same species. Thus, the α and β chain variable domain sequences present in dTCR polypeptide pair, or first and second segments of the scTCR polypeptide, may correspond to those of a first human TCR, and the α and β chain constant domain extracellular sequences may correspond to those of a second human TCR. For example, A6 Tax sTCR constant domain extracellular sequences can be used as a framework onto which heterologous α and β variable domains can be fused.

In one particular embodiment of the invention, the TCR α and β chain variable domain sequences present in the displayed dTCR polypeptide pair or first and second segments of the displayed scTCR polypeptide may together correspond to the functional variable domain of a first human TCR, and the TCR α and β chain constant domain extracellular sequences present in the dTCR polypeptide pair or first and second segments of the scTCR polypeptide may correspond to those of a second non-human TCR, Thus the α and β chain variable domain sequences present dTCR polypeptide pair or first and second segments of the scTCR polypeptide may correspond to those of a first human TCR, and the α and β chain constant domain extracellular sequences may correspond to those of a second non-human TCR. For example, murine TCR constant domain extracellular sequences can be used as a framework onto which heterologous human α and β TCR variable domains can be fused.

Linker in the scTCR Polypeptide

For displayed scTCRs, a linker sequence links the first and second TCR segments, to form a single polypeptide strand. The linker sequence may, for example, have the formula -P-AA-P- wherein P is proline and AA represents an amino acid sequence wherein the amino acids are glycine and serine.

For scTCRs to bind to a ligand, MHC-peptide complex in the case of αβ TCRs, the first and second segments are paired so that the variable domain sequences thereof are orientated for such binding. Hence the linker should have sufficient length to span the distance between the C terminus of the first segment and the N terminus of the second segment, or vice versa. On the other hand excessive linker length should preferably be avoided, in case the end of the linker at the N-terminal variable domain sequence blocks or reduces bonding of the scTCR to the target ligand.

For example, in the case where the constant domain extracellular sequences present in the first and second segments correspond to the constant domains of the α and β chains of a native TCR truncated at their C termini such that the cysteine residues which form the native interchain disulfide bond of the TCR are excluded, and the linker sequence links the C terminus of the first segment to the N terminus of the second segment.

The linker sequence may consist of, for example, from 26 to 41 amino acids, preferably 29, 30, 31 or 32 amino acids, or 33, 34, 35 or 36 amino acids. Particular linkers have the formula -PGGG-(SGGGG)$_5$-P- (SEQ ID NO: 1) and -PGGG-(SGGGG)$_6$-P-(SEQ ID NO:2) wherein P is proline, G is glycine and S is serine.

Inter-Chain Disulfide Bond dTCRs and scTCRs of the present invention may have a disulfide bond between the constant domain extracellular sequences of the dTCR polypeptide pair or first and second segments of the scTCR polypeptide. That bond may correspond to the native inter-chain disulfide bond present in native dimeric αβ TCRs, or may have no counterpart in native TCRs, being between cysteines specifically incorporated into the constant domain extracellular sequences of dTCR polypeptide pair or first and second segments of the scTCR polypeptide. In some cases, both a native and a non-native disulfide bond may be desirable.

As stated above, WO 03/020763 provides a detailed description of the methods required to introduce the specified non-native disulfide interchain bond and alternative residues between which it may be sited.

Required to prepare a library of mutated TCRs, are nucleic acids encoding (a) one chain of a dTCR polypeptide pair and (b) the other chain of a dTCR polypeptide pair fused to a nucleic acid sequence encoding a protein capable of forming part of the surface of a nucleoprotein particle; or nucleic acid encoding a scTCR polypeptide fused to a nucleic acid sequence encoding a protein capable of forming part of the surface of a nucleoprotein particle, the dTCR pair or scTCR.

For expression of TCRs host cells may be used transformed with an expression vector comprising nucleic acid encoding (a) one chain of a dTCR polypeptide pair and (b) the other chain of a dTCR polypeptide pair fused to a nucleic acid sequence encoding a protein capable of forming part of the surface of a nucleoprotein particle; or nucleic acid encoding a scTCR polypeptide fused to a nucleic acid sequence encoding a protein capable of forming part of the surface of a nucleoprotein particle, the dTCR pair or scTCR, Preferably the expression system comprises phagemid or phage genome vectors expressing nucleic acids (a) and (b). Preferably these phagemid or phage genome vectors is (are) those which encode bacteriophage gIII or gVIII coat proteins.

Transformed cells are incubated to allow the expression of the TCR-displaying nucleoprotein particles. These particles can then be used in assays to identify TCR variants with the desired affinity and/or off-rate characteristics. Any particles that possess the desired characteristics under investigation can then be isolated. The DNA encoding these TCRs can then be amplified by PCR and the sequence determined.

It is known that high expression levels of an exogenous polypeptide may be toxic to the host cell. In such cases, either a host strain which is more tolerant of the exogenous polypeptide must be found, or the expression levels in the host cell must be limited to a level which is tolerated. For example (Beekwilder et al., (1999) Gene 228 (1-2) 23-31) report that only mutated forms of a potato protease inhibitor (PI2) which contained deletions or amber stop codons would be successfully selected from a phage display library.

There are several strategies for limiting the expression levels of an exogenous polypeptide from a given expression system in a host which may be suitable for the limiting the expression levels of a scTCR, or one, or both TCR chains of a dTCR. These strategies are described in WO 2004/044004.

Correct pairing of scTCR polypeptide variable domain sequences after expression is preferably assisted by an introduced disulfide bond in the extracellular constant domain of the scTCR. Without wanting to be limited by theory, the novel disulfide bond is believed to provide extra stability to the scTCR during the folding process and thereby facilitating correct pairing of the first and second segments.

Also as mentioned above, for dTCR phage display, one of the dTCR polypeptide pair is expressed as if it were eventually to be displayed as a monomeric polypeptide on the phage, and the other of the dTCR polypeptide pair is co-expressed in the same host cell. As the phage particle self assembles, the two polypeptides self associate for display as a dimer on the phage. Again, in the preferred embodiment of this aspect of the invention, correct folding during association of the polypeptide pair is assisted by a disulfide bond between the constant sequences. Further details of a procedure for phage display of a dTCR having an interchain disulfide bond appear in the Examples contained within WO 2004/044004.

As an alternative, the phage displaying the first chain of the dTCR may be expressed first, and the second chain polypeptide may be contacted with the expressed phage in a subsequent step, for association as a functional dTCR on the phage surface.

The preferred in-vitro TCR display method for biopanning to identify TCRs comprising mutated CDR2 sequences having high affinity and/or slow off-rates for a target peptide-MHC complex is ribosomal display. Firstly, a DNA library is constructed that encodes a diverse array of mutated scTCRs or dTCR polypeptides using the techniques discussed above. The DNA library is then contacted with RNA polymerase in order to produce a complementary mRNA library. Optionally, for mRNA display techniques the mRNA sequences can then be ligated to a DNA sequence comprising a puromycin binding site. These genetic constructs are then contacted with ribosomes in-vitro under conditions allowing the translation of the scTCR polypeptide or the first polypeptide of the dTCR pair. In the case of the dTCR, the second of the polypeptide pairs is separately expressed and contacted with the ribosome-displayed first polypeptide, for association between the two, preferably assisted by the formation of the disulphide bond between constant domains. Alternatively, mRNA encoding both chains of the TCR may be contacted with ribosomes in-vitro under conditions allowing the translation of the TCR chains such that a ribosome displaying a dTCR is formed. These scTCR- or dTCR-displaying ribosomes can then used for screening or in assays to identify TCR variants with specific enhanced characteristics. Any particles that possess the enhanced characteristics under investigation can then be isolated. The mRNA encoding these TCRs can then converted to the complementary DNA sequences using reverse transcriptase. This DNA can then be amplified by PCR and the sequence determined.

scTCRs or dTCRs of the present invention may be displayed on nucleoprotein particles, for example phage particles, preferably filamentous phage particles, by, for example, the following two means:

(i) The C-terminus of one member of the dTCR polypeptide pair, or the C-terminus of the scTCR polypeptide, or the C-terminus of a short peptide linker attached to the C-terminus of either, can be directly linked by a peptide bond to a surface exposed residue of the nucleoprotein particle. For example, the said surface exposed residue is preferably at the N-terminus of the gene product of bacteriophage gene III or gene VIII; and (ii) The C-terminus of one member of the dTCR polypeptide pair, or the C-terminus of the scTCR polypeptide, or the C-terminus of a short peptide linker attached to the C-terminus of either, is linked by a disulfide bond to a surface exposed cysteine residue of the nucleoprotein particle via an introduced cysteine residue. For example, the said surface exposed residue is again preferably at the N-terminus of the gene product of bacteriophage gene III or gene VIII.

M13 and f1 are examples of bacteriophages that express gene III and gene VIII gene products.

Method (i) above is preferred. In the case of an scTCR, nucleic acid encoding the TCR may be fused to nucleic acid encoding the particle forming protein or a surface protein of the replicable particle such as a phage or cell. Alternatively, nucleic acid representing mRNA but without a stop codon, or fused to puromycin RNA may be translated by ribosome such that the TCR remains fused to the ribosome particle. In the case of a dTCR, nucleic acid encoding one chain of the TCR may be fused to nucleic acid encoding the particle forming protein or a cell surface protein of the replicable particle such as a phage or cell, and the second chain of the TCR polypeptide pair may be allowed to associate with the resultant expressed particle displaying the first chain. Proper functional association of the two chains may be assisted by the presence of cysteines in the constant domain of the two chains which are capable of forming an interchain disulfide bond, as more fully discussed below.

Isolation of TCR Variants with Increased Affinity for their Cognate Ligand

A specific embodiment of the invention is provided by a method for the purpose of determining the affinities and/or off-rates of library members which bind to the target pMHC and selecting those which have the desired affinities and/or off-rates, in which method (i) several members of the library are contacted in parallel with the target pMHC and members which bind to the pMHC are identified, (ii) members identified in step (i) are contacted in series with the target pMHC, and their affinities for the pMHC assessed, (iii) one or more members having the desired affinity determined in step (ii) are selected, and the CDR2 sequences of the displayed TCRs determined, (iv) soluble form TCRs incorporating the thus-determined CDR2 sequences, are created, (vi) the affinities and/or the off-rate for the target pMHC of these TCRs are redetermined and or determined as the case may be, and (vii) one or more TCRs having the desired affinity and/or off-rate determined in step (vi) are selected.

Additional Aspects

A scTCR or dTCR (which preferably is constituted by constant and variable sequences corresponding to human sequences) isolated by the method of the invention may be provided in substantially pure form, or as a purified or isolated preparation. For example, it may be provided in a form which is substantially free of other proteins.

The invention also provides a method for obtaining chain of a TCR selected by the method of this invention, which method comprises incubating a host cell comprising nucleic acid encoding that chain under conditions causing expression of the chain and then purifying said polypeptide chain. dTCRs can then be formed by refolding the purified α and β as described in Example 5.

Preferred features of each aspect of the invention are as for each of the other aspects mutatis mutandis. The prior art documents mentioned herein are incorporated to the fullest extent permitted by law,

EXAMPLES

The invention is fisher described in the following examples, which do not limit the scope of the invention in any way.

Reference is made in the following to the accompanying drawings in which:

FIGS. 1a and 1b show the DNA sequence of the α and β chains of the 1G4 TCR respectively (SEQ ID NOS:26 and 27). Each of these chains has a codon mutated to code for a cysteine residue. Shading indicates the location of these mutated codons.

FIGS. 2a and 2b show the amino acid sequences encoded by the DNA sequences of FIGS. 1a (SEQ ID NO:28) and 1b (SEQ ID NO:29) respectively. Shading indicates the location of these introduced cysteine residues.

FIG. 3 details the complete DNA sequence of phagemid plasmid pEX746:NY-ESO (SEQ ID NO:30).

FIG. 4 details the DNA sequence of the pEX922-1G4 plasmid (SEQ ID NO:31).

FIG. 5 details the DNA sequence of the pEX821 plasmid (SEQ ID NO:32).

FIG. 6 details the DNA sequence of the pEX954 plasmid (SEQ ID NO:33).

FIGS. 7a and 7b show respectively the DNA sequence of soluble versions of the ILA TCR α (SEQ ID NO:35) and β (SEQ ID NO:36) chains mutated to include additional cysteine residues to form a non-native disulphide bond. The mutated codon is indicated by shading.

FIGS. 8a and 8b show respectively the ILA TCR α (SEQ ID NO:38) and β (SEQ ID NO:39) chain extracellular amino acid sequences produced from the DNA sequences of FIGS. 7a and 7b. The introduced cysteine is indicated by shading.

FIGS. 9a and 9b show respectively the DNA sequence of soluble versions of an HIV Gag TCR α (SEQ ID NO:54) and β (SEQ ID NO:55) chains mutated to include additional cysteine residues to form a non-native disulfide bond. The mutated codon is indicated by shading.

FIGS. 10a and 10b show respectively an HIV Gag TCR α (SEQ ID NO:56) and β (SEQ ID NO:57) chain extracellular amino acid sequences produced from the DNA sequences of FIGS. 4a and 4b. The introduced cysteine is indicated by shading.

Example 1

1G4 CDR2 Library Construction

Multiple mutations were introduced separately into the CDR2α and CDR2β sequences of the 1G4 TCR chains in order to obtain two TCR libraries containing variants that bind the SLLMWITQC (SEQ ID NO: 3)-HLA-A*0201 complex with increased affinity and/or decreased off-rate for this pMHC.

A highly diverse population of mutants was obtained for each CDR2 sequence using PCR amplification with mutagenic oligonucleotides (Jon342 & Jon344) as forward primers and downstream fully complementary oligonucleotides as reverse primers to generate a population of mutated fragments. In the case of CDR2α three of the core residues were randomised (Jon342) whereas for CDR2β, four residues were randomised (Jon344).

In order to introduce convenient restriction sites for subsequent library construction, each of the two resulting mutagenised PCR fragments are joined to an additional fragment comprising an adjacent part of the TCR open reading frame with overlapping complementarity to the 5' region of the mutagenic oligonucleotide. This splicing reaction, termed Splicing by Overlap Extension (SOE), is carried out in a second PCR reaction using the appropriate flanking forward and reverse primer pair.

PCR1—Generation of Mutagenised CDR2α Fragments:

38.5 µl water, 5 µl 10×PCR buffer, 1.5 µl Jon342 primer (10 µM stock), 1.5 µl CDR1bRev primer (10 µM stock), 2.5 ng of a template vector containing 1G4 TCR α and β chains (pEX746:NY-ESO), 2 ul dNTPs (20 mM combined stock), 1 µl pfu turbo polymerase. The PCR reaction was subjected to an initial denaturation of 2 min at 95 degrees, followed by 30 cycles of 95 degrees for 30 sec, 53 degrees for 30 sec and 72 degrees for 60 sec. A final elongation step of 72 degrees for 10 min was included. The entire 50 µl PCR reaction was resolved on a 1.4% TBE agarose gel and the band representing the mutagenised product was excised and purified using the Qiagen MinElute kit according to the manufacturers instructions.

FIGS. 1a and 1b show the DNA sequence of the α and β chains of the 1G4 TCR respectively. Each of these chains has a codon mutated to code for a cysteine residue. Shading indicates the location of these mutated codons.

FIGS. 2a and 2b show the amino acid sequences encoded by the DNA sequences of FIG. 1a and 1b respectively. Shading indicates the location of these introduced cysteine residues.

FIG. 3 details the DNA sequence of the pEX746: NY-ESO plasmid

PCR2—Generation of Mutagenised CDR2 β Fragments:

As above substituting the primers Jon344 and Yol22.

PCR3—Generation of Overlapping Fragment for CDR2α Mutations:

As above substituting the primers Yol13 and CDR2aRev.

PCR4—Generation of Overlapping Fragment for CDR2β Mutations:

As above substituting the primers CDR2aFw and CDR2bRev.

PCR5—Generation of Spliced PCR/PCR3 CDR2 αMutagenised Fragment:

The purified template fragments from PCR1 and PCR3 were diluted 1:10 in water and 1 µl of each was combined in a 50 µl PCR reaction that also comprised 37 µl water, 5 µl 10×PCR buffer, 1.5 µl Yol13 primer (10 µM stock), 1.5 µl cdr1bRev primer (10 µM stock), 2 ul dNTPs (20 mM combined stock), 1 µl pfu turbo polymerase. The splicing PCR reaction was subjected to an initial denaturation of 2 min at 95° C., followed by 27 cycles of 95° C. for 30 sec, 54° C. for 40 sec and 72° C. for 90 sec. A final elongation step of 72° C. for 10 min was included. Twelve identical PCR reactions were carried out. The twelve PCR reactions were pooled and the spliced mutagenised product was purified using the Qiagen Qiaquick kit according to the manufacturers instructions.

PCR6—Generation of Spliced PCR2/PCR4 CDR2, Mutagenised Fragment:

As above substituting PCR2 and PCR4.

The mutagenised products of PCR5 were digested with Nco I and BssH II and ligated into the pEX922-1G4 phage display vector (FIG. 4 details the DNA sequence of this plasmid), also digested with Nco I and BssH II, containing the parental 1G4 TCR open reading frame, thus resulting in the substitution of the parental CDR2 α sequence motif for a large and diverse population of mutant sequences. The same was performed for PCR6 such that a large and diverse population of CDR2 β mutant sequences were substituted for the parental sequence. In this case however, the cloning enzymes used were BssH II and Not I.

Ligations were carried out at a 3:1 insert to vector ratio using T4 DNA ligase according to standard protocols.

The ligated CDR2α and CDR2β mutant pools were independently electroporated into TG1 cells following concentration and desalting on Qiagen MinElute columns. Electroporation was performed according to the protocols provided by the commercial supplier of the cells (Stratagene) and using ratios of approximately 300 ng DNA per 50 µl electrocompetent cells. Two electroporations were performed for each of the two libraries. Following electroporation, cells were reclaimed from cuvettes by resuspension in 950 µl of pre-warmed (37° C.) SOC medium and allowed to recover by gentle agitation in a 50 ml sterile tube for 40 min. Subsequently, 1 ml of recovered cells was added to 50 mls of 2TY medium (16 g Bacto-tryptone, 10 g Bacto-yeast extract, 5 g NaCl per liter) containing 100 µg/ml ampicillin and 1.6% glucose (2TYAG) in a sterile shake flask ie. two flasks per library. Flasks were shaken for 5 hr at 37° C. at 280 rpm, after which time the cultures had achieved an $OD_{600}$ of 1-1.5. Cells were collected by centrifugation and resuspended in 4 ml/library of 2TY+20% glycerol. Aliquots (250 µl) were frozen on dry ice and stored at −80° C.

Wherein:

N=A, T, G or C

K=G or T

Example 2

Isolation of High Affinity 1G4 TCRs Comprising Mutated CDR2 Sequences

The isolation of high affinity 1G4 TCRs comprising mutated CDR2 sequences was carried out from a population of phage particles comprising a pool of the two libraries constructed as described in Example 1. The initial panning was carried as follows utilising the selection of phage particles displaying mutant 1G4 TCRs capable of binding to SLLMWITQC (SEQ ID NO:3)-HLA-A*0201 complex in solution.

Streptavidin-coated paramagnetic beads (Dynal M280) were pre-washed according to manufacturer's protocols. Phage particles, displaying mutated 1G4 TCR at a concentration of $10^{12}$ to $10^{13}$ cfu, were pre-mixed with biotinylated SLLMWITQC (SEQ ID NO:3)-HLA-A*0201 complex at concentrations of $1\times10^{-7}$M for all three rounds of selection carried out. The mixture of 1G4 TCR-displaying phage particles and SLLMWITQC (SEQ ID NO:3)-HLA-A*0201 complex was incubated for one hour at room temperature with gentle rotation, and 1G4 TCR-displaying phage particles bound to biotinylated SLLMWITQC (SEQ ID NO:3)-HLA-A*0201 complex were captured using 100 µl of streptavidin-coated M280 magnetic beads for all three rounds. After capture of the phage particles, the beads were washed a total of six times (three times in PBStween20 and three times in PBS) using a Dynal magnetic particle concentrator. After final wash, the beads were re-suspended in 100 µl of freshly prepared PBS and 50 µl of the re-suspended beads was used to infect 10 ml of E. coli TG1 at OD(600 nm)=0.5 freshly prepared for the amplification of the selected phage particles according to established methods.

After the third round of selection, 300 colonies were picked from the plates and used to inoculate 100 µl of 2TYAG in a

```
Primers:
Jon342
5'-GTCTCACATCTCTGTTGCTTATTNNKNNKNNKCAGAGAGAGCAAACAAGTGGAAG-3'      (SEQ ID NO: 4)

Jon344
5'-GCTGAGGCTGATTCATTACTCANNKNNKNNKNNKATCACTGACCAAGGAGAAGTCC-3'    (SEQ ID NO: 5)

CDR2aRev
5'-AATAAGCAACAGAGATGTGAGAC-3'                                     (SEQ ID NO: 6)

CDR2aFw
5'-CAGAGAGAGCAAACAAGTGGAAG-3'                                     (SEQ ID NO: 7)

CDR2bRev
5'-TGAGTAATGAATCAGCCTCAGC-3'                                      (SEQ ID NO: 8)

CDR1bRev
5'-CATATCCTGGGCACACTGCAG-3'                                       (SEQ ID NO: 9)

Yol13
5'-TCACACAGGAAACAGCTATG-3'                                        (SEQ ID NO: 10)

Yol22
5'-CATTTTCAGGGATAGCAAGC-3'                                        (SEQ ID NO: 11)
```

96-well microtiter plate. The culture was incubated at 30° C. with shaking overnight. 100 µl of 2TYAG was then sub-inoculated with 2 to 5 µl of the overnight cultures, and incubated at 30° C. with shaking for 2 to 3 hours or until the culture became cloudy. To infect the cells with helper phage, the culture was infected with 100 µl of 2TYAG containing 5×10$^9$ pfu helper phages, and incubated at 37° C. for 60 minutes. 5 µl of the infected culture was added to 200 µl of 2TYAK ("TYAG+100 µg/ml Ampicillin and 50 µg/ml Kanomycin) The plates were incubated at 25° C. for 20 to 36 hours with shaking at 300 rpm. The cells were precipitated by centrifugation at 3000 g for 10 minutes at 4° C. Supernatants were used to screen for high affinity 1G4 TCR mutants by phage ELSA as follows.

Example 3

Primary and Competition ELISA Analysis of the Binding of Native and Mutated Disulphide-Linked CDR2 Mutant 1G4 TCRs Displayed on Phage Particles The following primary ELISA assay using disulfide-linked native 1G4 TCRs and 1G4 TCRs comprising mutated CDR2 sequences displayed on the phage particles was used to assess the affinity of these molecules for the SLLMWITQC (SEQ ID NO:3)-HLA-A*0201 complex.

Nunc-Immuno Maxisorp wells coated with Neutravidin were rinsed twice with PBS. 25 µL 5 µg/ml biotinylated SLLMWITQC (SEQ ID NO:3)-HLA-A*0201 complex was added to each well and these were incubated at room temperature for 30 to 60 minutes, and followed by two PBS rinses. Non-specific protein binding sites in the wells were blocked by the addition of 300 µl 3% skimmed milk in PBS followed by incubation at room temperature for 2 hours. In order to prepare phage particles displaying the mutant 1G4 TCRs produced as detailed in Example 2, the phage particles were mixed with 3% skimmed milk in PBS, followed by incubation at room temperature for 1 hour. The phage is added to the wells coated with SLLMWITQC (SEQ ID NO:3)-HLA-A*0201 and incubated at room temperature for 1 hour, followed by 3 washes with PBS containing 0.1% tween 20 and then 3 washes with PBS. The bound TCR-displaying phage particles are detected in a two-step reaction using primary anti-fd polyclonal antisera followed by alkaline phosphatase conjugated anti-rabbit monoclonal antibodies (Sigma).

The phage-displayed TCRs that bound to the SLLMWITQC (SEQ ID NO:3)-HLA-A*0201 complex in this primary ELISA assay were then sequenced to characterise the nature of the CDR2 mutations. Phagemid clones of interest were then subjected to a competition ELISA assay in order to provide further information on the affinity of these TCRs for the SLLMWITQC (SEQ ID NO:3)-HLA-A*0201 complex.

The competition ELISA assay was carried out exactly as describe above for the primary ELSA assay except: In order to prepare phage particles displaying the mutant 1G4 TCRs, phage particles were mixed with 3% skimmed milk in PBS and 100 µl or 200 µl of the soluble SLLMWITQC (SEQ ID NO:3)-HLA-A*0201 complex followed by incubation at room temperature for 1 hour.

The degree of inhibition of binding that occurs for a given addition of soluble SLLMWITQC (SEQ ID NO:3)-HLA-A*0201 is proportional to the affinity of the TCR for the SLLMWITQC (SEQ ID NO:3)-HLA-A*0201 complex.

Results

The following table details the CDR2 sequences of 20 primary ELISA-positive hits obtained from the Round 3 pannings described in this example.

| α CDR2 Sequence | β CDR2 Sequence | Frequency (No. of wells containing this TCR Sequence) |
|---|---|---|
| IQSSQR (native) (SEQ ID NO:12) | SVGAGI (native) (SEQ ID NO:13) | 0 |
| IPFWQR (SEQ ID NO:20) | SVGAGI (native) (SEQ ID NO:13) | 2 |
| ITPWQR (SEQ ID NO:16) | SVGAGI (native) (SEQ ID NO:13) | 1 |
| IMPWQR (SEQ ID NO:47) | SVGAGI (native) (SEQ ID NO:13) | 1 |
| IGPYQR (SEQ ID NO:48) | SVGAGI (native) (SEQ ID NO:13) | 1 |
| IQGWQR (SEQ ID NO:17) | SVGAGI (native) (SEQ ID NO:13) | 1* |
| IQGHQR (SEQ ID NO:49) | SVGAGI (native) (SEQ ID NO:13) | 1* |
| IMGTQR (SEQ ID NO:19) | SVGAGI (native) (SEQ ID NO:13) | 2 |
| IQSSQR (native) (SEQ ID NO:12) | SVSVGM (SEQ ID NO:14) | 8 |
| IQSSQR (native) (SEQ ID NO:12) | SVAIQT (SEQ ID NO:21) | 3 |

*-The mutated glutamine in this CDR2α sequence was encoded by an amber codon, which results in the expression of a glutamine.

The following table details the competition ELISA data obtained for the phage-displayed WT and dominant mutant 1G4 TCRs identified by the primary ELISA. The mutant 1G4 TCRs comprised native variable domain sequences except for mutations in one of the CDR2 sequences.

| α CDR2 Sequence | β CDR2 Sequence | % Binding Inhibition 200 nM Sol. pMHC |
|---|---|---|
| IQSSQR (native) (SEQ ID NO:12) | SVGAGI (native) (SEQ ID NO:13) | 0 |
| IQSSQR (SEQ ID NO:12) | SVSVGM (SEQ ID NO:14) | 78 |
| IPFWQR (SEQ ID NO:20) | SVGAGI (SEQ ID NO:13) | 69 |
| IQSSQR (SEQ ID NO:12) | SVAIQT (SEQ ID NO:21) | 92 |

Example 4

Second Generation Libraries Using Discrete CDR2 Hits of Interest

The three phagemid clones encoding high affinity 1G4 TCR containing mutations in either the CDR2α or CDR2α sequences that were characterised by the competitive ELISA assay of Example 3 were further mutated. This was carried out by using these clones as the starting templates for the construction of second generation libraries These libraries were constructed using the PCR approach described in Example 1 to mutate the WT CDR2 sequence in each clone.

The isolation of high affinity 1G4 TCRs comprising doubly-mutated CDR2 sequences was carried out from a population of phage particles comprising a pool of the three libraries constructed as described above. Three rounds of panning were performed as described in Example 2 except that the concentration of biotinylated SLLMWITQC (SEQ ID NO:3)-HLA-A*0201 used was 1×10$^{-8}$M.

Hits were identified and characterised as described in Example 3.

Results

The following table details the sequences of 20 primary ELISA-positive hits obtained from the second generation Round 3 pannings described in this example.

| α CDR2 Sequence | β CDR2 Sequence | Frequency (No. of wells containing this TCR) |
|---|---|---|
| IQSSQR (native) (SEQ ID NO.12) | SVSVGM (SEQ ID NO:14) | 0 |
| ISPWQR (SEQ ID NO:15) | SVSVGM (SEQ ID NO:14) | 3 |
| ITPWQR (SEQ ID NO:16) | SVSVGM (SEQ ID NO:14) | 1$^A$ |
| IHPWQR (SEQ ID NO:50) | SVSVGM (SEQ ID NO:14) | |
| IMGWQR (SEQ ID NO:51) | SVSVGM (SEQ ID NO:14) | 1 |
| IQGWQR (SEQ ID NO:17) | SVSVGM (SEQ ID NO:14) | 6*$^A$ |
| IPGWQR (SEQ ID NO:52) | SVSVGM (SEQ ID NO:14) | 1 |
| IMGTQR (SEQ ID NO:19) | SVSVGM (SEQ ID NO:14) | 4$^A$ |
| IMGHQR (SEQ ID NO:18) | SVSVGM (SEQ ID NO:14) | 1 |
| IQGHQR (SEQ ID NO:49) | SVSVGM (SEQ ID NO:14) | 2**$^A$ |

All CDR2α mutants identified by this ELISA assay were found to contain the SVSVGM (SEQ ID NO:14) CDR2β sequence.

*-The mutated glutamine in 5 of these CDR2α sequences was encoded by an amber codon, which results in the expression of a glutamine residue.

**-The mutated glutamine in both these CDR2α sequences was encoded by an amber codon, which results in the expression of a glutamine residue.

$^A$-indicates a mutant 1G4 TCR sequence that excately matches one of those recovered from the 1$^{st}$ generation experiment described in Examples 1-3.

The following table details the competition ELISA data obtained for the phage-displayed WT and double-mutant 1G4 TCRs. The mutant 1G4 TCRs comprised native variable domain sequences except for mutations in both of the CDR2 sequences

| α CDR2 Sequence | β CDR2 Sequence | % Binding Inhibition 100 nM Sol. pMHC |
|---|---|---|
| IQSSQR (native) (SEQ ID NO:12) | SVGAGI (native) (SEQ ID NO:13) | 0 |
| ISPWQR (SEQ ID NO:15) | SVSVGM (SEQ ID NO:14) | 96/87 |
| ITPWQR (SEQ ID NO:16) | SVSVGM (SEQ ID NO:14) | 96 |
| IQGWQR (SEQ ID NO:17) | SVSVGM (SEQ ID NO:14) | 95 |
| IMGHQR (SEQ ID NO:18) | SVSVGM (SEQ ID NO:14) | 95 |
| IMGTQR (SEQ ID NO:19) | SVSVGM (SEQ ID NO:14) | 94 |

Example 5

Production of Soluble High Affinity Disulfide Linked 1G4 TCRs Comprising Mutated CDR2 Sequences from Phagemids Phagemid DNA encoding the high affinity 1G4 TCR mutants identified as described in Example 3 was isolated from the relevant *E. coli* cells using a Mini-Prep kit (Qiagen, UK)

PCR amplification was carried out using the phagemid DNA as template and the following primers to amplify the soluble TCR α and β chain DNA sequences.

```
1G4 TCR α forward primer TRAV21
5-GCCGGCCATGGCCAAACAGGAGGTGACGCAGATTCCT-3           (SEQ ID NO: 22)
(ClaI restriction site is underlined)

Universal TCR α reverse primer
5-TTG TCA GTC GAC TTA GAG TCT CTC AGC TGG TAC ACG-3  (SEQ ID NO: 23)
(Sal I restriction site is underlined)

1G4 TCR β chain forward primer TRBV6-1/2/3/5/6/7/8/9
5-TCACAGCGCGCAGGCTGGTGTCACTCAGACCCCAAA-3            (SEQ ID NO: 24)
(AseI restriction site is underlined)

Universal beta chain reverse primer
5-tagaaaccggtggccaggcacaccagtgtggc-3                (SEQ ID NO: 25)
(AgeI restriction site is underlined)
```

PCR was carried out using the following conditions: 50 ng plasmid template, 1 µl of 10 mM dNTP, 5 µl of 10×pfu-buffer, 25 pmol of fwd primer, 25 µmol of rev primer, 1 µl pfu in total volume 50 µl. After an initial denaturation step of 2 mins at 95° C., the reaction was subjected to 25 cycles of denaturation (95° C., 10 secs), annealing (55° C. 10 secs), and elongation (72° C., 2 mins).

In order to produce a disulfide-linker version of the high affinity 1G4 TCRs the beta chain PCR product was then digested with Age1/Ase1 and cloned into pEX821 (FIG. 5 details the DNA of this plasmid for Sequence) cut with Nde/Age1. The alpha chain PCR product was digested with ClaI/SalI and cloned into pEX954 (FIG. 6 details the DNA sequence of this plasmid) cut ClaI/XhoI. The DNA sequences of the mutated soluble 1G4 TCR α and β chains were verified by automated sequencing.

Example 6

Expression, Refolding and Purification of Soluble TCR

The expression plasmids containing the TCR α-chain and β-chain respectively as prepared in Example 5 were transformed separately into *E. coli* strain BL21pLysS, and single ampicillin-resistant colonies were grown at 37° C. in TYP (ampicillin 100 µg/ml) medium to $OD_{600}$ of 0.4 before inducing protein expression with 0.5 mM IPTG. Cells were harvested three hours post-induction by centrifugation for 30 minutes at 400 rpm in a Beckman J-6B. Cell pellets were re-suspended in a buffer containing 50 mM Tris-HCl, 25% (w/v) sucrose, 1 mM NAEDTA, 0.1% (w/v) NaAzide, 10 mM DTT, pH 8.0. After an overnight freeze-thaw step, re-suspended cells were sonicated in 1 minute bursts for a total of around 10 minutes in a Milsonix XL2020 sonicator using a standard 12 mm diameter probe. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl, 0.5% Triton-X100, 200 mM NaCl, 10 mM NaEDTA, 0.1% (w/v) NaAzide, 2 mM DTT, pH 8.0) before being pelleted by centrifugation for 15 minutes at 1300 rpm in a Beckman J2-21. Detergent and salt was then removed by a similar wash in the following buffer: 50 mM Tris-HCl, 1 mM NaEDTA, 0.1% (w/v) NaAzide, 2 mM DTT, pH 8.0. Finally, the inclusion bodies were divided into 30 mg aliquots and frozen at −70° C. Inclusion body protein yield was quantitated by solubilising with 6M guanidine-HCl and measurement with a Bradford dye-binding assay (PerBio).

Approximately 30 mg of TCR β chain and 60 mg of TCR α chain solubilised inclusion bodies were thawed from frozen stocks, samples were then mixed and the mixture diluted into 15 ml of a guanidine solution (6 M Guanidine-hydrochloride, 10 mM Sodium Acetate, 10 mM EDTA), to ensure complete chain de-naturation. The guanidine solution containing fully reduced and denatured TCR chains was then injected into 1 liter of the following refolding buffer: 100 mM Tris pH 8.5, 400 mM L-Arginine, 2 mM EDTA, 5 mM reduced Glutathione, 0.5 mM oxidised Glutathione, 5M urea, 0.2 mM PMSF. The redox couple (2-mercaptoethylamine and cystamine (to final concentrations of 6.6 mM and 3.7 mM, respectively) were added approximately 5 minutes before addition of the denatured TCR chains. The solution was left for 5 hrs+15 minutes. The refolded TCR was dialysed in Spectrapor 1 membrane (Spectrum; Product No. 132670) against 10 L 10 mM Tris pH 8.1 at 5° C.±3° C. for 18-20 hours. After this time, the dialysis buffer was changed to fresh 10 mM Tris pH 8.1 (10 L) and dialysis was continued at 5° C.±3° C. for another 20-22 hours.

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia). Peak fractions were stored at 4° C. and analysed by Coomassie-stained SDS-PAGE before being pooled and concentrated. Finally, the sTCR was purified and characterised using a Superdex 200HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa was pooled and concentrated prior to characterisation by Biacore surface plasmon resonance analysis.

Example 7

Biacore Surface Plasmon Resonance Characterisation of sTCR Binding to Specific pMHC A surface plasmon resonance biosensor (Biacore 3000™) was used to analyse the binding of a sTCR to its peptide-MHC ligand. This was facilitated by producing single pMHC complexes (described below) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

Such immobilised complexes are capable of binding both T-cell receptors and the coreceptor CD8αα, both of which may be injected in the soluble phase. Specific binding of TCR is obtained even at low concentrations (at least 40 μg/ml), implying the TCR is relatively stable. The pMHC binding properties of sTCR are observed to be qualitatively and quantitatively similar if sTCR is used either in the soluble or immobilised phase. This is an important control for partial activity of soluble species and also suggests that biotinylated pMHC complexes are biologically as active as non-biotinylated complexes.

The interactions between 1G4 sTCR containing a novel inter-chain bond and its ligand/MHC complex or an irrelevant HLA-peptide combination, the production of which is described above, were analysed on a BIAcore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the individual HLA-peptide complexes in separate flow cells via binding between the biotin cross linked onto β2m and streptavidin which have been chemically cross linked to the activated surface of the flow cells. The assay was then performed by passing sTCR over the surfaces of the different flow cells at a constant flow rate, measuring the SPR response in doing so.

Serial dilutions of WT IG4 sTCR were prepared and injected at constant flow rate of 5 μl min-1 over two different flow cells; one coated with ~1000 RU of the specific SLLM-WITQC (SEQ ID NO:3-HLA-A*0201 complex, the second coated with ~1000 RU of non-specific HLA-A2-peptide complex. Response was normalised for each concentration using the measurement from the control cell. Normalised data response was plotted versus concentration of TCR sample and fitted to a hyperbola in order to calculate the equilibrium binding constant, $K_D$. (Price & Dwek, Principles and Problems in Physical Chemistry for Biochemists ($2^{nd}$ Edition) 1979, Clarendon Press, Oxford).

To Measure Kinetic Parameters

For high affinity TCRs $K_D$ was determined by experimentally measuring the dissociation rate constant, kd, and the association rate constant, ka. The equilibrium constant $K_D$ was calculated as kd/ka.

TCR was injected over two different cells one coated with ~300 RU of specific SLLMWITQC (SEQ ID NO:3)-HLA-A*0201 complex, the second coated with ~300 RU of non-specific HLA-A2-peptide complex. Flow rate was set at 50 μl/min. Typically 250 μl of TCR at ~3 μM concentration was injected. Buffer was then flowed over until the response had returned to baseline. Kinetic parameters were calculated using Biaevaluation software. The dissociation phase was also fitted to a single exponential decay equation enabling calculation of half-life.

Results

The interaction between a soluble disulfide-linked native 1G4 TCR and the SLLMWITQC (SEQ ID NO:3)-HLA-A*0201 complex was analysed using the above methods and demonstrated a $K_D$ of 15 μM and a $k_{off}$ of $1.28 \times 10^{-1}$ $S^{-1}$.

The following table details the Biacore results obtained using the above methods for the high affinity 1G4 TCR with mutated CDR2 sequences:

| α CDR2 Sequence | β CDR2 Sequence | $K_D$ nM | $k_{off}$ $S^{-1}$ | Half-life Minutes |
|---|---|---|---|---|
| IQSSQR (Native) (SEQ ID NO: 12) | SVGAGI (Native) (SEQ ID NO: 13) | 15,000 | $1.28 \times 10^{-1}$ | 0.17 |
| IPFWQR (SEQ ID NO: 20) | SVSVGM (SEQ ID NO: 14) | 1-10 | $2.37 \times 10^{-4}$ | 5.6 |

Example 8

ILA TCR CDR2 Library Construction

The methods described in the previous examples can be modified to produce and test high affinity variants of other TCRs comprising mutated CDR2 sequences. Briefly, DNA encoding the TCR chain to be mutated is used as a template to produce the CDR2 libraries as described in Example 1. The only alteration required is that the primers utilised in the library construction must be complementary to the equivalent part of the DNA sequence of the TCR chain to be mutated.

These methods have been applied to produce and test variants of the ILA TCR which specifically binds to the ILAK-FLHWL (SEQ ID NO: 34)-HLA-A*0201 pMHC.

The DNA sequences of the α and β TCR chains of a soluble variant of the ILA TCR comprising the native variable domains and introduced cysteine codons are provided in FIGS. 7a and 7b (SEQ ID NOs: 35 and 36) respectively.

The amino acid sequences of the α and β TCR chains of a soluble variant of the ILA TCR comprising the native variable domains and introduced cysteine residues are provided in FIGS. 8a and 8b (SEQ ID NOs: 37 and 38) respectively.

Multiple mutations were introduced into the CDR2α and CDR2β sequences of the ILA TCR chains in order to obtain TCR libraries containing variants that bind the ILAKFLHWL (SEQ ID NO: 34) -HLA-A*0201 complex with increased affinity and/or decreased off-rate for this pMHC. As the ILA TCR β Chain is based on the same TRBV6.5 gene as the 1G4 TCR β Chain and amino acid and DNA sequence is identical in, and around, the CDR2 β region of these two TCRs very similar primers were used to mutate the ILA TCR CDR2β sequence.

A highly diverse population of mutants was obtained for each CDR2 sequence using PCR amplification with mutagenic oligonucleotides (ILA TCR equivalents of Jon342 & Jon344) as forward primers and downstream fully complementary oligonucleotides as reverse primers to generate a population of mutated fragments. In the case of CDR2α three of the core residues were randomised (ILA TCR equivalent of Jon342) whereas for CDR2β, four residues were randomised (ILA TCR equivalent of Jon344).

In order to introduce convenient restriction sites for subsequent library construction, each of the two resulting mutagenised PCR fragments are joined to an additional fragment comprising an adjacent part of the TCR open reading frame with overlapping complementarity to the 5' region of the mutagenic oligonucleotide. This splicing reaction, termed Splicing by Overlap Extension (SOE), is carried out in a second PCR reaction using the appropriate flanking forward and reverse primer pair.

PCR1—Generation of Mutagenised CDR2α Fragments:

38.5 µl water, 5 µl 10×PCR buffer, 1.5 µl ILA TCR equivalent of Jon342 primer (10 µM stock), 1.5 µl ILA TCR equivalent of CDR1bRev primer (10 µM stock), 2.5 ng of a template vector containing ILA TCR α and β chains (pEX746:ILA), 2 ul dNTPs (20 mM combined stock), 1 µl pfu turbo polymerase. The PCR reaction was subjected to an initial denaturation of 2 min at 95 degrees, followed by 30 cycles of 95 degrees for 30 sec, 53 degrees for 30 sec and 72 degrees for 60 sec. A final elongation step of 72 degrees for 10 min was included. The entire 50 µl PCR reaction was resolved on a 1.4% TBE agarose gel and the band representing the mutagenised product was excised and purified using the Qiagen MinElute kit according to the manufacturers instructions.

PCR2—Generation of Mutagenised CDR2 β Fragments:

As above substituting the primers ILA TCR equivalents of Jon344 and Yol22.

PCR3—Generation of Overlapping Fragment for CDR2 α Mutations:

As above substituting the primers ILA TCR equivalents of Yol13 and CDR2aRev.

PCR4—Generation of Overlapping Fragment for CDR2β Mutations:

As above substituting the primers ILA TCR equivalents of CDR2aFw and CDR2bRev.

PCR5—Generation of Spliced PCR1/PCR3 CDR2 α Mutagenised Fragment:

The purified template fragments from PCR1 and PCR3 were diluted 1:10 in water and 1 µl of each was combined in a 50 µl PCR reaction that also comprised 37 µl water, 5 µl 10×PCR buffer, 1.51 µl ILA TCR equivalent of Yol13 primer (10 µM stock), 1.5 µl ILA TCR equivalents of cdr1bRev primer (10 µM stock), 2 ul dNTPs (20 mM combined stock), 1 µl pfu turbo polymerase. The splicing PCR reaction was subjected to an initial denaturation of 2 min at 95° C., followed by 27 cycles of 95° C. for 30 sec, 54° C. for 40 sec and 72° C. for 90 sec. A final elongation step of 72° C. for 10 min was included. Twelve identical PCR reactions were carried out. The twelve PCR reactions were pooled and the spliced mutagenised product was purified using the Qiagen Qiaquick kit according to the manufacturers instructions.

PCR6—Generation of Spliced PCR2/PCR4 CDR2 β Mutagenised Fragment:

As above substituting PCR2 and PCR4.

The mutagenised products of PCR5 were digested with Nco I and BssH II and ligated into the pEX922-ILA phage display vector, also digested with Nco I and BssH II, containing the parental ILA TCR open reading frame, thus resulting in the substitution of the parental CDR2 α sequence motif for a large and diverse population of mutant sequences. The same was performed for PCR6 such that a large and diverse population of CDR2 β mutant sequences were substituted for the parental sequence. In this case however, the cloning enzymes used were BssH II and Not I. Ligations were carried out at a 3:1 insert to vector ratio using T4 DNA ligase according to standard protocols.

The ligated CDR2α and CDR2β mutant pools were independently electroporated into TG1 cells following concentration and desalting on Qiagen MinElute columns. Electroporation was performed according to the protocols provided by the commercial supplier of the cells (Stratagene) and using ratios of approximately 300 ng DNA per 50 µl electrocompetent cells. Two electroporations were performed for each of the two libraries. Following electroporation, cells were reclaimed from cuvettes by resuspension in 950 µl of pre-warmed (37° C.) SOC medium and allowed to recover by gentle agitation in a 50 ml sterile tube for 40 min. Subsequently, 1 ml of recovered cells was added to 50 mls of 2TY medium (16 g Bacto-tryptone, 10 g Bacto-yeast extract, 5 g NaCl per liter) containing 100 µg/ml ampicillin and 1.6% glucose (2TYAG) in a sterile shake flask ie. two flasks per library. Flasks were shaken for 5 hr at 37° C. at 280 rpm, after which time the cultures had achieved an $OD_{600}$ of 1-1.5. Cells were collected by centrifugation and resuspended in 4 ml/library of 2TY+20% glycerol. Aliquots (250 µl) were frozen on dry ice and stored at −80° C.

The ILA TCR libraries prepared above were then panned and tested using the methods described for the IG4 TCR CDR2 mutants in Examples 2 and 3 above except that the cognate pMHC for the ILA TCR (ILAKFLHWL (SEQ ID NO: 34) HLA-A*0201) was used for the panning and subsequent ELISA testing.

Results

| ILA TCR α CDR2 Sequence | ILA TCR β CDR2 Sequence | % Binding Inhibition 20 nM Sol. pMHC | % Binding Inhibition 100 nM Sol. pMHC | % Binding Inhibition 200 nM Sol. pMHC |
|---|---|---|---|---|
| IPSG (native) (SEQ ID NO: 39) | SVGAGI (native) (SEQ ID NO: 40) | 0 | 0 | 0 |
| IPSG (native) (SEQ ID NO: 39) | SIHPEY (SEQ ID NO: 41) | 91 | 98 | 96 |
| IPSG (native) (SEQ ID NO: 39) | SLHPSV (SEQ JD NO: 42) | 68 | | 96 |
| IPSG (native) (SEQ ID NO: 39) | SICPSC (SEQ ID NO: 43) | 94 | 97 | 94 |
| IPSG (native) (SEQ ID NO: 39) | SICWGC (SEQ ID NO: 44) | 79 | | 92 |

-continued

| ILA TCR α CDR2 Sequence | ILA TCR β CDR2 Sequence | % Binding Inhibition 20 nM Sol. pMHC | % Binding Inhibition 100 nM Sol. pMHC | % Binding Inhibition 200 nM Sol. pMHC |
|---|---|---|---|---|
| IPSG (native) (SEQ ID NO: 39) | SIWEFE (SEQ ID NO: 45) | 88 | 91 | 95 |
| IPSG (native) (SEQ ID NO: 39) | SRWVGD (SEQ ID NO: 46) | 77 | 94 | 95 |

Soluble ILA TCRs comprising the CDR2 mutations identified by the ELISA method as described in Example 3 were then produced using the methods as describe in Examples 5 and 6 to allow Biacore characterisation of the mutants using the methods described in Example 7.

Example 9

High Affinity HIV Gag TCR CDR2 Mutants

As noted above, the methods described in the previous examples can be modified to produce and test high affinity variants of other TCRs comprising mutated CDR2 sequences. Briefly, DNA encoding the TCR chain to be mutated is used as a template to produce the CDR2 libraries as described in Example 1. The only alteration required is that the primers utilised in the library construction must be complementary to the equivalent part of the DNA sequence of the TCR chain to be mutated.

These methods have been applied to produce and test variants of a parental HIV Gag TCR which specifically binds to the SLYNTVATL (SEQ ID NO: 53) -HLA-A*0201 pMHC.

The DNA sequences of the α and β TCR chains of a soluble variant of the ILA TCR comprising the native variable domains and introduced cysteine codons are provided in FIGS. 9a and 9b (SEQ ID NOs: 54 and 55) respectively.

The amino acid sequences of the α and βTCR chains of a soluble variant of the ILA TCR comprising the native variable domains and introduced cysteine residues are provided in FIGS. 10a and 10b (SEQ ID NOs: 56 and 57) respectively.

Multiple mutations were introduced into the CDR2α and CDR2β sequences of the parental HIV Gag TCR chains in order to obtain TCR libraries containing variants that bind the SLYNTVATL (SEQ ID NO: 53) -HLA-A*0201 complex with increased affinity and/or decreased off-rate for this pMHC.

A highly diverse population of mutants was obtained for each CDR2 sequence using PCR amplification with mutagenic oligonucleotides.

In order to introduce convenient restriction sites for subsequent library construction, each of the two resulting mutagenised PCR fragments are joined to an additional fragment comprising an adjacent part of the TCR open reading frame with overlapping complementarity to the 5' region of the mutagenic oligonucleotide. This splicing reaction, termed Splicing by Overlap Extension (SOE), is carried out in a second PCR reaction using the appropriate flanking forward and reverse primer pair.

The ligated CDR2α and CDR2β mutant pools were independently electroporated into TG1 cells following concentration and desalting on Qiagen MinElute columns. Electroporation was performed according to the protocols provided by the commercial supplier of the cells (Stratagene) and using ratios of approximately 300 ng DNA per 50 μl electrocompetent cells. Two electroporations were performed for each of the two libraries. Following electroporation, cells were reclaimed from cuvettes by resuspension in 950 μl of prewarmed (37° C.) SOC medium and allowed to recover by gentle agitation in a 50 ml sterile tube for 40 min. Subsequently, 1 ml of recovered cells was added to 50 mls of 2TY medium (16 g Bacto-tryptone, 10 g Bacto-yeast extract, 5 g. NaCl per liter) containing 100 μg/ml ampicillin and 1.6% glucose (2TYAG) in a sterile shake flask ie. two flasks per library. Flasks were shaken for 5 hr at 37° C. at 280 rpm, after which time the cultures had achieved an $OD_{600}$ of 1-1.5. Cells were collected by centrifugation and resuspended in 4 ml/library of 2TY+20% glycerol. Aliquots (250 μl) were frozen on dry ice and stored at −80° C.

The HIV Gag TCR libraries prepared above were then panned and tested using the methods described for the IG4 TCR CDR2 mutants in Examples 2 and 3 above except that the cognate pMHC for the HIV Gag TCR (SLYNTVATL (SEQ ID NO: 53) HLA-A*021) was used for the panning and subsequent ELISA.

Soluble disulfide-linked TCRs containing the CDR2 mutations identified were then produced to allow Biacore-based determinations of their respective affinities for the SLYNTVATL (SEQ ID NO:53)-HLA-A*0201 ligand.

Results

Note that all the high affinity HIV Gag TCRs identified from the above libraries contained only CDR2β mutations

| HIV Gag TCR α CDR2 Sequence | HIV Gag TCR β CDR2 Sequence | Kon (1/Ms) | Koff (1/s) | Kd (nM) |
|---|---|---|---|---|
| IYSNG (parental) (SEQ ID NO: 58) | YYEEEE (parental) (SEQ ID NO: 59) | | | 141 nM |
| IYSNG (parental) (SEQ ID NO: 58) | YVRGVE (SEQ ID NO: 60) | 8.6e4 | 4.6e-4 | 5.3 nM |
| IYSNG (parental) (SEQ ID NO: 58) | YALGEE (SEQ ID NO: 61) | 1.2e5 | 8.3e-4 | 7.1 nM |

The invention claimed is:

1. A method of increasing the affinity and/or decreasing the off-rate of a given TCR specific for a given target pMHC, comprising creating a plurality of TCRs having an α chain CDR2 sequence and/or a β chain CDR2 sequence different from the corresponding CDR2 sequence(s) of the given TCR but having the same α and β CDR1 and CDR3 sequences as the given TCR, determining the affinity and/or off-rate of members of said plurality of TCRs for the target pMHC, and selecting one or more members having at least a 10-fold greater affinity for the target pMHC than the given TCR and/or a 10-fold slower off-rate for the target pMHC than the given TCR.

2. The method of claim 1, comprising:
(a) creating a first plurality of TCRs which, relative to the given TCR, are mutated in the α chain CDR2 sequence but not the β chain CDR2 sequence,
(b) separately creating a second plurality of TCRs which, relative to the given TCR, are mutated in the β chain CDR2 sequence but not the α chain CDR2 sequence,
(c) determining the affinity and/or off-rate of members of said first and second pluralities of TCRs for the target pMHC, and selecting one or more members of each plurality having at least a 10-fold greater affinity for the target pMHC than the given TCR and/or a 10-fold slower off-rate for the target pMHC than the given TCR,
(d) determining the CDR2 sequences of the selected members of each plurality,
(e) creating one or more TCRs each having an α chain CDR2 sequence of the first plurality and a β chain CDR2 sequence of the second plurality, and
(f) determining the affinity and/or off-rate of the TCR or TCRs created in step (e) for the target pMHC, and selecting one or more thereof having at least a 10-fold greater affinity for the target pMHC than the given TCR and/or a 10-fold slower off-rate for the target pMHC than the given TCR.

3. The method of claim 1, comprising:
(a) providing nucleic acid coding for both the β and β chains of the given TCR,
(b) subjecting said nucleic acid to mutagenesis of one or more codons of the α chain CDR2 sequence and one or more codons of the β chain CDR2 sequence,
(c) from the mutated nucleic acid of step (b) creating a plurality of TCRs which, relative to the given TCR, are mutated in one or more amino acids of the α chain CDR2 sequence and one or more amino acids of the β chain CDR2 sequence, and
(d) determining the affinity and/or off-rate of members of said plurality of TCRs for the target pMHC, and selecting one or more members having at least a 10-fold greater affinity for the target pMHC than the given TCR and/or a 10-fold slower off-rate for the target pMHC than the given TCR.

4. The method of claim 3 wherein in step (b) the said nucleic acid is subjected to mutagenesis of up to three consecutive codons of the α chain CDR2 sequence and up to three consecutive codons of the β chain CDR2 sequence, and in step (c) a plurality of TCRs is created which, relative to the given TCR, are mutated in up to 3 consecutive amino acids of the α chain CDR2 sequence and up to three consecutive amino acids of the β chain CDR2 sequence.

5. The method of claim 1 wherein the said affinities and/or off-rates are determined by Surface Plasmon Resonance.

6. The method of claim 1 wherein one or more TCRs having at least a 100-fold greater affinity and/or 100-fold slower off-rate for the target pMHC than the given TCR is/are selected.

7. The method of claim 1 wherein one or more TCRs having at least a 500-fold greater affinity and/or 500-fold slower off-rate for the target pMHC than the given TCR is/are selected.

8. The method of claim 1 wherein the TCRs for affinity and/or on/off rate determination are created in soluble form.

9. The method of claim 1 wherein the TCRs for affinity and on/off rate determination are created as a diverse library of phage-displayed αβ dimeric TCRs.

10. The method of claim 9 wherein the phage-displayed αβ dimeric TCRs comprise
- a first polypeptide wherein a sequence corresponding to a TCR α chain variable domain sequence is fused to the N terminus of a sequence corresponding to a TCR α chain constant domain extracellular sequence, and
- a second polypeptide wherein a sequence corresponding to a TCR β chain variable domain sequence fused to the N terminus a sequence corresponding to a TCR β chain constant domain extracellular sequence, the first and second polypeptides being linked by a disulfide bond which has no equivalent in native αβ T cell receptors, and one of said first or second polypeptides being linked by a peptide bond at its C-terminus to a surface exposed amino acid residue of the phage particle.

11. The method of claim 9 wherein the phage-displayed αβ dimeric TCRs comprise
- a first polypeptide wherein a sequence corresponding to a TCR α chain variable domain sequence is fused to the N terminus of a sequence corresponding to a TCR α chain constant domain extracellular sequence, and
- a second polypeptide wherein a sequence corresponding to a TCR β chain variable domain sequence is fused to the N terminus a sequence corresponding to a TCR β chain constant domain extracellular sequence, the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof, one of said first or second polypeptides being linked by a peptide bond at its C-terminus to a surface exposed amino acid residue of the phage particle.

12. The method of claim 1 wherein said plurality of TCRs is created as a diverse library of ribosome-displayed αβ single chain TCRs.

13. The method of claim 9 wherein, for the purpose of determining the affinities and/or off-rates of library members which bind to the target pMHC and selecting those which have the desired affinities and/or off-rates
- (i) several members of the library are contacted in parallel with the target pMHC and members which bind to the pMHC are identified,
- (ii) members identified in step (i) are contacted in series with the target pMHC, and their affinities for the pMHC assessed,
- (iii) one or more members having the desired affinity assessed in step (ii) are selected, and the CDR2 sequences of the displayed TCRs determined,
- (iv) soluble form TCRs incorporating the thus-determined CDR2 sequences, are created,
- (vi) the affinities and/or the off-rate for the target pMHC of these TCRs are redetermined and or determined as the case may be, and
- (vii) one or more TCRs having the desired affinity and/or off-rate determined in step (vi) are selected.

* * * * *

UNITED STATES PATENT AND TRADEMARK OFFICE
CERTIFICATE OF CORRECTION

| | |
|---|---|
| PATENT NO. | : 7,608,410 B2 |
| APPLICATION NO. | : 12/246607 |
| DATED | : October 27, 2009 |
| INVENTOR(S) | : Dunn et al. |

It is certified that error appears in the above-identified patent and that said Letters Patent is hereby corrected as shown below:

column 74, line 31: "â and â" is replaced with "á and â"

Signed and Sealed this

Fifteenth Day of December, 2009

David J. Kappos
*Director of the United States Patent and Trademark Office*

SEQUENCE LISTING

<160> NUMBER OF SEQ ID NOS: 61

<210> SEQ ID NO 1
<211> LENGTH: 30
<212> TYPE: PRT
<213> ORGANISM: Artificial Sequence
<220> FEATURE:
<223> OTHER INFORMATION: Short scTCR Linker

<400> SEQUENCE: 1

Pro Gly Gly Gly Ser Gly Gly Gly Ser Gly Gly Gly Gly Ser Gly
1               5                   10                  15

Gly Gly Ser Gly Gly Gly Gly Ser Gly Gly Gly Gly Pro
        20                  25                  30

<210> SEQ ID NO 2
<211> LENGTH: 35
<212> TYPE: PRT
<213> ORGANISM: Artificial Sequence
<220> FEATURE:
<223> OTHER INFORMATION: Long scTCR Linker

<400> SEQUENCE: 2

Pro Gly Gly Gly Ser Gly Gly Gly Gly Ser Gly Gly Gly Ser Gly
1               5                   10                  15

Gly Gly Ser Gly Gly Gly Gly Ser Gly Gly Gly Gly Ser Gly Gly
        20                  25                  30

Gly Gly Pro
35

<210> SEQ ID NO 3
<211> LENGTH: 9
<212> TYPE: PRT
<213> ORGANISM: Homo sapiens

<400> SEQUENCE: 3

Ser Leu Leu Met Trp Ile Thr Gln Cys
1               5

<210> SEQ ID NO 4
<211> LENGTH: 55
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(55)
<223> OTHER INFORMATION: Wherein:
      N = A, T, G or C
      K = G or T

<400> SEQUENCE: 4
gtctcacatc tctgttgctt attnnknnkn nkcagagaga gcaaacaagt ggaag        55

<210> SEQ ID NO 5
<211> LENGTH: 56
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(56)
<223> OTHER INFORMATION: Wherein:

```
        N = A, T, G or C
        K = G or T

<400> SEQUENCE: 5
gctgaggctg attcattact cannknnknn knnkatcact gaccaaggag aagtcc      56

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
aataagcaac agagatgtga gac                                          23

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cagagagagc aaacaagtgg aag                                          23

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tgagtaatga atcagcctca gc                                           22

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
catatcctgg gcacactgca g                                            21

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tcacacagga aacagctatg                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cattttcagg gatagcaagc                                              20
```

```
<210> SEQ ID NO 12
<211> LENGTH: 6
<212> TYPE: PRT
<213> ORGANISM: Homo sapiens

<400> SEQUENCE: 12

Ile Gln Ser Ser Gln Arg
1               5

<210> SEQ ID NO 13
<211> LENGTH: 6
<212> TYPE: PRT
<213> ORGANISM: Homo sapiens

<400> SEQUENCE: 13

Ser Val Gly Ala Gly Ile
1               5

<210> SEQ ID NO 14
<211> LENGTH: 6
<212> TYPE: PRT
<213> ORGANISM: Artificial Sequence
<220> FEATURE:
<223> OTHER INFORMATION: Mutated 1G4 TCR CDR2 Beta loop

<400> SEQUENCE: 14

Ser Val Ser Val Gly Met
1               5

<210> SEQ ID NO 15
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 15

Ile Ser Pro Trp Gln Arg
1               5

<210> SEQ ID NO 16
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 16

Ile Thr Pro Trp Gln Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 17

Ile Gln Gly Trp Gln Arg
1               5

<210> SEQ ID NO 18
<211> LENGTH: 6
<212> TYPE: PRT
<213> ORGANISM: Artificial Sequence
```

```
<220> FEATURE:
<223> OTHER INFORMATION: Mutated 1G4 TCR CDR2 Alpha loop

<400> SEQUENCE: 18

Ile Met Gly His Gln Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 19

Ile Met Gly Thr Gln Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 20

Ile Pro Phe Trp Gln Arg
1               5

<210> SEQ ID NO 21
<211> LENGTH: 6
<212> TYPE: PRT
<213> ORGANISM: Artificial Sequence
<220> FEATURE:
<223> OTHER INFORMATION: Mutated 1G4 TCR CDR2 Beta loop

<400> SEQUENCE: 21

Ser Val Ala Ile Gln Thr
1               5

<210> SEQ ID NO 22
<211> LENGTH: 37
<212> TYPE: DNA
<213> ORGANISM: Artificial Sequence
<220> FEATURE:
<223> OTHER INFORMATION: Primer

<400> SEQUENCE: 22
gccggccatg gccaaacagg aggtgacgca gattcct                              37

<210> SEQ ID NO 23
<211> LENGTH: 36
<212> TYPE: DNA
<213> ORGANISM: Artificial Sequence
<220> FEATURE:
<223> OTHER INFORMATION: Primer

<400> SEQUENCE: 23
ttgtcagtcg acttagagtc tctcagctgg tacacg                               36

<210> SEQ ID NO 24
<211> LENGTH: 36
<212> TYPE: DNA
<213> ORGANISM: Artificial Sequence
<220> FEATURE:
<223> OTHER INFORMATION: Primer
```

```
<400> SEQUENCE: 24
tcacagcgcg caggctggtg tcactcagac cccaaa                              36

<210> SEQ ID NO 25
<211> LENGTH: 32
<212> TYPE: DNA
<213> ORGANISM: Artificial Sequence
<220> FEATURE:
<223> OTHER INFORMATION: Primer

<400> SEQUENCE: 25
tagaaaccgg tggccaggca caccagtgtg gc                                  32

<210> SEQ ID NO 26
<211> LENGTH: 627
<212> TYPE: DNA
<213> ORGANISM: Artificial Sequence
<220> FEATURE:
<223> OTHER INFORMATION: DNA encoding the alpha chain of a soluble
      DiS-linked 1G4 TCR

<400> SEQUENCE: 26
atgcaggagg ygacacagat tcctgcagct ctgagtgtcc cagaaggaga aaacttggtt    60
ctcaactgca gtttcactga tagcgctatt tacaacctcc agtggttag gcaggaccct    120 gggaaaggtc tcacatctct gttgcttatt cagtcaagtc agagagagca aacaagtgga   180
agacttaatg cctcgctgga taaatcatca ggacgtagta ctttatacat tgcagcttct   240
cagcctggtg actcagccac ctacctctgt gctgtgaggc ccacatcagg aggaagctac   300
atacctacat ttggaagagg aaccagcctt attgttcatc cgtatatcca gaaccctgac   360
cctgccgtgt accagctgag agactctaaa tccagtgaca gtctgtctg cctattcacc    420 gattttgatt ctcaaacaaa tgtgtcacaa gtaaggatt ctgatgtgta tcacagac     480 aaatgtgtgc tagacatgag gtctatggac ttcaagagca cagtgctgt ggcctggagc    540 aacaaatctg actttgcatg tgcaaacgcc ttcaacaaca gcattattcc agaagacacc   600
ttcttcccca gcccagaaag ttcctaa                                       627

<210> SEQ ID NO 27
<211> LENGTH: 729
<212> TYPE: DNA
<213> ORGANISM: Artificial Sequence
<220> FEATURE:
<223> OTHER INFORMATION: DNA encoding the beta chain of a soluble
      DiS-linked 1G4 TCR

<400> SEQUENCE: 27
atgggtgtca ctcagacccc aaaattccag gtcctgaaga caggacagag catgacactg    60
cagtgtgccc aggatatgaa ccatgaatac atgtcctggt atcgacaaga cccaggcatg   120
gggctgaggc tgattcatta ctcagttggt gctggtatca ctgaccaagg agaagtcccc   180
aatggctaca atgtctccag atcaaccaca gaggatttcc cgctcaggct gctgtcggct   240 gctcctccc agacatctgt gtacttctgt gccagcagtt acgtcgggaa caccggggag    300 ctgtttttg agaaggctc taggctgacc gtactggagg acctgaaaaa cgtgttccca    360
cccgaggtcg ctgtgtttga gccatcagaa gcagagatct cccacaccca aaaggccaca   420
ctggtgtgcc tggccacagg cttctacccc gaccacgtgg agctgagctg gtgggtgaat   480
gggaaggagg tgcacagtgg ggtctgcaca gacccgcagc ccctcaagga gcagcccgcc   540
ctcaatgact ccagatacgc tctgagcagc cgcctgaggg tctcggccac cttctggcag   600
```

```
gacccccgca accacttccg ctgtcaagtc cagttctacg ggctctcgga gaatgacgag    660
tggacccagg atagggccaa accgtcacc cagatcgtca gcgccgaggc ctggggtaga   720
gcagactaa                                                           729
```

<210> SEQ ID NO 28
<211> LENGTH: 208
<212> TYPE: PRT
<213> ORGANISM: Artificial Sequence
<220> FEATURE:
<223> OTHER INFORMATION: Alpha chain of a soluble DiS-linked 1G4 TCR

<400> SEQUENCE: 28

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205
```

<210> SEQ ID NO 29
<211> LENGTH: 242
<212> TYPE: PRT
<213> ORGANISM: Artificial Sequence
<220> FEATURE:
<223> OTHER INFORMATION: Beta chain of a soluble DiS-linked 1G4 TCR

<400> SEQUENCE: 29

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
```

Ala Pro Ser Gln Thr Ser Val Tyr Phe Cys Ala Ser Ser Tyr Val Gly
 85                  90                  95

Asn Thr Gly Glu Leu Phe Phe Gly Glu Gly Ser Arg Leu Thr Val Leu
100                 105                 110

Glu Asp Leu Lys Asn Val Phe Pro Pro Glu Val Ala Val Phe Glu Pro
115                 120                 125

Ser Glu Ala Glu Ile Ser His Thr Gln Lys Ala Thr Leu Val Cys Leu
130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
165                 170                 175

Glu Gln Pro Ala Leu Asn Asp Ser Arg Tyr Ala Leu Ser Ser Arg Leu
180                 185                 190

Arg Val Ser Ala Thr Phe Trp Gln Asp Pro Arg Asn His Phe Arg Cys
195                 200                 205

Gln Val Gln Phe Tyr Gly Leu Ser Glu Asn Asp Glu Trp Thr Gln Asp
210                 215                 220

Arg Ala Lys Pro Val Thr Gln Ile Val Ser Ala Glu Ala Trp Gly Arg
225                 230                 235                 240

Ala Asp

<210> SEQ ID NO 30
<211> LENGTH: 5495
<212> TYPE: DNA
<213> ORGANISM: Artificial Sequence
<220> FEATURE:
<223> OTHER INFORMATION: pEX746: NY-ESO Vector

<400> SEQUENCE: 30

```
gttaactacg tcaggtggca cttttcgggg aaatgtgcgc ggaacccctat ttgtttatt      60 tttctaaaata cattcaaata tgtatccgct catgagacaa taaccctgat aaatgcttca     120
ataatattga aaaggaaga gtatgagtat tcaacatttc cgtgtcgccc ttattccctt      180
ttttgcggca ttttgccttc ctgtttttgc tcacccagaa acgctggtga agtaaaaga      240 tgctgaagat cagttgggtg cacgagtggg ttacatcgaa ctggatctca acagcggtaa     300
gatccttgag agttttcgcc ccgaagaacg ttctccaatg atgagcactt ttaaagttct     360
gctatgtggc gcggtattat cccgtgttga cgccgggcaa gagcaactcg gtcgccgcat    420
acactattct cagaatgact tggttgagta ctcaccagtc acagaaaagc atcttacgga    480
tggcatgaca gtaagagaat tatgcagtgc tgccataacc atgagtgata acactgcggc    540
caacttactt ctgacaacga tcggaggacc gaaggagcta accgcttttt tgcacaacat    600
gggggatcat gtaactcgcc ttgatcgttg ggaaccggag ctgaatgaag ccataccaaa    660
cgacgagcgt gacaccacga tgcctgtagc aatggcaaca acgttgcgca aactattaac    720
tggcgaacta cttactctag cttcccggca acaattaata gactggatgg aggcggataa    780
agttgcagga ccacttctgc gctcggccct tccggctggc tggtttattg ctgataaatc    840
tggagccggt gagcgtgggt ctcgcggtat cattgcagca ctggggccag atggtaagcc    900
ctcccgtatc gtagttatct acacgacggg gagtcaggca actatggatg aacgaaatag    960
acagatcgct gagataggtg cctcactgat taagcattgg taactgtcag accaagttta   1020
ctcatatata ctttagattg atttaccccg gttgataatc agaaaagccc caaaaacagg    1080
```

```
aagattgtat aagcaaatat ttaaattgta aacgttaata ttttgttaaa attcgcgtta    1140
aatttttgtt aaatcagctc atttttaac caataggccg aaatcggcaa aatcccttat     1200
aaatcaaaag aatagcccga gatagggttg agtgttgttc cagtttggaa caagagtcca    1260
ctattaaaga acgtggactc caacgtcaaa gggcgaaaaa ccgtctatca gggcgatggc    1320
ccactacgtg aaccatcacc caaatcaagt tttttgggt cgaggtgccg taaagcacta     1380
aatcggaacc ctaaagggag ccccgatttt agagcttgac ggggaaagcg aacgtggcga    1440
gaaaggaagg gaagaaagcg aaaggagcgg gcgctagggc gctggcaagt gtagcggtca    1500
cgctgcgcgt aaccaccaca cccgccgcgc ttaatgcgcc gctacagggc gcgtaaaagg    1560
atctaggtga agatccttt tgataatctc atgaccaaaa tcccttaacg tgagttttcg     1620
ttccactgag cgtcagaccc cgtagaaaag atcaaaggat cttcttgaga tcctttttt    1680 ctgcgcgtaa tctgctgctt gcaaacaaaa aaccaccgc taccagcggt ggtttgtttg     1740
ccggatcaag agctaccaac tctttttccg aaggtaactg gcttcagcag agcgcagata    1800
ccaaatactg ttcttctagt gtagccgtag ttaggccacc acttcaagaa ctctgtagca    1860
ccgcctacat acctcgctct gctaatcctg ttaccagtgg ctgctgccag tggcgataag    1920
tcgtgtctta ccgggttgga ctcaagacga tagttaccgg ataaggcgca gcggtcgggc    1980
tgaacggggg gttcgtgcac acagcccagc ttggagcgaa cgacctacac cgaactgaga    2040
tacctacagc gtgagctatg agaaagcgcc acgcttcccg aagggagaaa ggcggacagg    2100
tatccggtaa gcggcagggt cggaacagga gagcgcacga gggagcttcc aggggggaaac   2160 gcctggtatc tttatagtcc tgtcgggttt cgccacctct gacttgagcg tcgattttg     2220 tgatgctcgt cagggggcgc gagcctatgg aaaaacgcca gcaacgcggc cttttacgg     2280 ttcctggcct tttgctggcc ttttgctcac atgtaatgtg agttagctca ctcattaggc    2340
accccaggct ttacactta tgcttccggc tcgtatgttg tgtggaattg tgagcggata     2400
acaatttcac acaggaaaca gctatgacca tgattacgcc aagctacgta cttaagtatt    2460
ctatttcaag gagacagtca taatgaaata cctattgcct acggcagccg ctggattgtt    2520
attactcgcg gcccagccgg ccatggccaa acaggaggtg acgcagattc ctgcagctct    2580
gagtgtccca gaaggagaaa acttggttct caactgcagt ttcactgata gcgctattta    2640
caacctccag tggtttaggc aggaccctgg gaaaggtctc acatctctgt tgcttattca    2700
gtcaagtcag agagagcaaa caagtggaag acttaatgcc tcgctggata aatcatcagg    2760
acgtagtact ttatacattg cagcttctca gcctggtgac tcagccacct acctctgtgc    2820
tgtgaggccc acatcaggag gaagctacat acctacattt ggaagaggaa ccagccttat    2880
tgttcatccg tatatccaga acccggatcc tgccgtgtac cagctgagag actctaaatc    2940
cagtgacaag tctgtctgcc tattcaccga ttttgattct caaacaaatg tgtcacaaag    3000
taaggattct gatgtgtata tcacagacaa atgtgtgcta gacatgaggt ctatggactt    3060
caagagcaac agtgctgtgg cctggagcaa caaatctgac tttgcatgtg caaacgcctt    3120
caacaacagc attattccag aagacacctt cttccccagc ccagaaagtt cctaataacc    3180
taggttaatt aagaattctt taagaagggg atatacatat gaaaaaatta ttattcgcaa    3240
ttcctttagt tgttcctttc tattctcaca gcgcgcaggc tggtgtcact cagacccaa     3300 aattccaggt cctgaagaca ggacagagca tgacactgca gtgtgcccag gatatgaacc    3360
atgaatacat gtcctggtat cgacaagacc caggcatggg gctgaggctg attcattact   3420
```

```
cagttggtgc tggtatcact gaccaaggag aagtccccaa tggctacaat gtctccagat    3480
caaccacaga ggatttcccg ctcaggctgc tgtcggctgc tccctcccag acatctgtgt    3540
acttctgtgc cagcagttac gtcgggaaca ccggggagct gttttttgga gaaggctcta    3600
ggctgaccgt actggaggac ctgaaaaacg tgttcccacc cgaggtcgct gtgtttgagc    3660
catcagaagc agagatctcc cacacccaaa aggccacact ggtgtgcctg gccacaggct    3720
tctaccccga ccacgtggag ctgagctggt gggtgaatgg gaaggaggtg cacagtgggg    3780
tctgcacaga cccgcagccc ctcaaggagc agcccgccct caatgactcc agatacgctc    3840
tgagcagccg cctgagggtc tcggccacct tctggcagga cccccgcaac cacttccgct    3900
gtcaagtcca gttctacggg ctctcggaga tgacgagtg acccaggat agggccaaac     3960 ccgtcaccca gatcgtcagc gccgaggcct ggggtagagc agacgcggcc gcatctagaa    4020
ttcaccatca tcactagact gttgaaagtt gtttagcaaa accccataca gaaaattcat    4080
ttactaacgt ctggaaagac gacaaaactt tagatcgtta cgctaactat gagggttgtc    4140
tgtggaatgc tacaggcgtt gtagtttgta ctggtgacga aactcagtgt tacggtacat    4200
gggttcctat tgggcttgct atccctgaaa atgagggtgg tggctctgag ggtggcggtt    4260
ctgagggtgg cggttctgag ggtggcggta ctaaacctcc tgagtacggt gatacaccta    4320
ttccgggcta tacttatatc aaccctctcg acggcactta tccgcctggt actgagcaaa    4380
accccgctaa tcctaatcct tctcttgagg agtctcagcc tcttaatact ttcatgtttc    4440
agaataatag gttccgaaat aggcaggggg cattaactgt ttatacgggc actgttactc    4500
aaggcactga ccccgttaaa acttattacc agtacactcc tgtatcatca aaagccatgt    4560
atgacgctta ctggaacggt aaattcagag actgcgcttt ccattctggc tttaatgagg    4620
atccattcgt ttgtgaatat caaggccaat cgtctgacct gcctcaacct cctgtcaatg    4680
ctggcggcgg ctctggtggt ggttctggtg gcggctctga gggtggtggc tctgagggtg    4740
gcggttctga gggtggcggc tctgaggag gcggttccgg tggtggctct ggttccggtg    4800
attttgatta tgaaaagatg gcaaacgcta ataagggggc tatgaccgaa aatgccgatg    4860
aaaacgcgct acagtctgac gctaaaggca aacttgattc tgtcgctact gattacggtg    4920
ctgctatcga tggtttcatt ggtgacgttt ccggccttgc taatggtaat ggtgctactg    4980
gtgattttgc tggctctaat cccaaatggc tcaagtcgg tgacggtgat aattcacctt    5040
taatgaataa tttccgtcaa tatttacctt ccctccctca atcggttgaa tgtcgccctt    5100
ttgtctttag cgctggtaaa ccatatgaat tttctattga ttgtgacaaa ataaacttat    5160
tccgtggtgt ctttgcgttt cttttatatg ttgccacctt tatgtatgta ttttctacgt    5220
ttgctaacat actgcgtaat aaggagtctt aataaggtac cctctagtca aggcctatag    5280
tgagtcgtat tacggactgg ccgtcgtttt acaacgtcgt gactgggaaa accctggcgt    5340
tacccaactt aatcgccttg cagcacatcc ccctttcgcc agctggcgta atagcgaaga    5400
ggcccgcacc gatcgccctt cccaacagtt gcgcagcctg aatggcgaat ggcgcttcgc    5460
ttggtaataa agcccgcttc ggcgggcttt ttttt                              5495
```

<210> SEQ ID NO 31
<211> LENGTH: 6277
<212> TYPE: DNA
<213> ORGANISM: Artificial Sequence
<220> FEATURE:
<223> OTHER INFORMATION: pEX922 1G4 Vector

<400> SEQUENCE: 31

-continued

```
ttttttttgt tgcctgctag cgatccaagc aatatccgta tgtctgcggg tatcgcatta      60
caatggatgt ccccattggg gccgttggtg ttctcctacg cccagccgtt caaaaagtac     120
gatggagaca aggcagaaca gttccagttt aacatcggta aaacctggta agtgttctcc     180
gcaaaggaat gtagtggtag tgtagcgatg actttaggcg atcaatataa gatcgccggg     240
ccacgcaaag aactgcaccc tccggtgcaa atgggatggt aaggagttta ttgtgaaaaa     300
gtggttatta gctgcaggtc tcggtttagc actggcaact tctgctcagg cggctgacaa     360
aattgcaatc gtcaacatgg gcagcctgtt ccagcaggta gcgcagaaaa ccggtgtttc     420
taacacgctg gaaaatgagt caaaggccg tgccagcgaa ctgcagcgta tggaaaccga     480
tctgcaggct aaaatgaaaa agctgcagtc catgaaagcg ggcagcgatc gcactaagct     540
ggaaaaagac gtgatggctc agcgccagac ttttgctcag aaagcgcagg cttttgagca     600
ggatcgcgca cgtcgttcca acgaagaacg cggcaaactg gttactcgta tccagactgc     660
tgtgaaatcc gttgccaaca gccaggatat cgatctggtt gttgatgcaa acgccgttgc     720
ttacaacagc agcgatgtaa aagacatcac tgccgacgta ctgaaacagg ttaaataaac     780
tagtagtagg aactacgtca ggtggcactt ttcggggaaa tgtgcgcgga cccctatt      840 gtttattttt ctaaatacat tcaaatatgt atccgctcat gagacaataa ccctgataaa     900
tgcttcaata atattgaaaa aggaagagta tgagtattca acatttccgt gtcgccctta     960
ttcccttttt tgcggcattt tgccttcctg ttttttgctca cccagaaacg ctggtgaaag    1020
taaaagatgc tgaagatcag ttgggtgcac gagtgggtta catcgaactg gatctcaaca    1080
gcggtaagat ccttgagagt tttcgccccg aagaacgttc tccaatgatg agcacttta    1140 aagttctgct atgtggcgcg gtattatccc gtgttgacgc cgggcaagag caactcggtc    1200
gccgcataca ctattctcag aatgacttgg ttgagtactc accagtcaca gaaaagcatc    1260
ttacggatgg catgacagta agagaattat gcagtgctgc cataaccatg agtgataaca    1320
ctgcggccaa cttacttctg acaacgatcg gaggaccgaa ggagctaacc gcttttttgc    1380
acaacatggg ggatcatgta actcgccttg atcgttggga accggagctg aatgaagcca    1440
taccaaacga cgagcgtgac accacgatgc ctgtagcaat ggcaacaacg ttgcgcaaac    1500
tattaactgg cgaactactt actctagctt cccggcaaca attaatagac tggatggagg    1560
cggataaagt tgcaggacca cttctgcgct cggcccttcc ggctggctgg tttattgctg    1620
ataaatctgg agccggtgag cgtgggtctc gcggtatcat tgcagcactg gggccagatg    1680
gtaagccctc ccgtatcgta gttatctaca cgacggggag tcaggcaact atggatgaac    1740
gaaatagaca gatcgctgag ataggtgcct cactgattaa gcattggtaa ctgtcagacc    1800
aagtttactc atatatactt tagattgatt taccccggtt gataatcaga aaagccccaa    1860
aaacaggaag attgtataag caaatattta aattgtaaac gttaatattt tgttaaaatt    1920
cgcgttaaat ttttgttaaa tcagctcatt ttttaaccaa taggccgaaa tcggcaaaat    1980
cccttataaa tcaaaagaat agcccgagat agggttgagt gttgttccag tttggaacaa    2040
gagtccacta ttaaagaacg tggactccaa cgtcaaaggg cgaaaaaccg tctatcaggg    2100
cgatggccca ctacgtgaac catcacccaa atcaagtttt ttggggtcga ggtgccgtaa    2160
agcactaaat cggaacccta agggagcccc cgatttaga gcttgacggg gaaagcgaac    2220
gtggcgagaa aggaagggaa gaaagcgaaa ggagcgggcg ctaggcgct ggcaagtgta     2280 gcggtcacgc tgcgcgtaac caccacaccc gccgcgctta atgcgccgct acagggcgcg    2340
```

-continued

```
taaaaggatc taggtgaaga tccttttga taatctcatg accaaaatcc cttaacgtga  2400
gttttcgttc cactgagcgt cagacccgt agaaagatc aaggatctt cttgagatcc  2460 ttttttctg cgcgtaatct gctgcttgca acaaaaaaa ccaccgctac cagcggtggt  2520
ttgtttgccg gatcaagagc taccaactct ttttccgaag gtaactggct tcagcagagc  2580
gcagatacca atactgttc ttctagtgta gccgtagtta ggccaccact tcaagaactc  2640
tgtagcaccg cctacatacc tcgctctgct aatcctgtta ccagtggctg ctgccagtgg  2700
cgataagtcg tgtcttaccg ggttggactc aagacgatag ttaccggata aggcgcagcg  2760
gtcgggctga cgggggggtt cgtgcacaca gcccagcttg gagcgaacga cctacaccga  2820
actgagatac ctacagcgtg agctatgaga aagcgccacg cttcccgaag ggagaaaggc  2880
ggacaggtat ccggtaagcg cagggtcgg aacaggagag cgcacgaggg agcttccagg  2940
gggaaacgcc tggtatcttt atagtcctgt cgggtttcgc cacctctgac ttgagcgtcg  3000
atttttgtga tgctcgtcag ggggggcggag cctatggaaa aacgccagca acgcggcctt  3060
tttacggttc ctggcctttt gctggccttt tgctcacatg taatgtgagt tagctcactc  3120
attaggcacc ccaggcttta cactttatgc ttccggctcg tatgttgtgt ggaattgtga  3180
gcggataaca atttcacaca ggaaacagct atgaccatga ttacgccaag ctacgtactt  3240
aagtattcta tttcaaggag acagtcataa tgaaatacct attgcctacg cagccgctg  3300 gattgttatt actcgcggcc cagccggcca tggccaaaca ggaggtgacg cagattcctg  3360
cagctctgag tgtcccagaa ggagaaaact tggttctcaa ctgcagtttc actgatagcg  3420
ctatttacaa cctccagtgg tttaggcagg accctgggaa aggtctcaca tctctgttgc  3480
ttattcagtc aagtcagaga gagcaaacaa gtggaagact taatgcctcg ctggataaat  3540
catcaggacg tagtacttta tacattgcag cttctcagcc tggtgactca gccacctacc  3600
tctgtgctgt gaggcccaca tcaggaggaa gctacatacc tacatttgga agaggaacca  3660
gccttattgt tcatccgtat atccagaacc cggatcctgc cgtgtaccag ctgagagact  3720
ctaaatccag tgacaagtct gtctgcctat tcaccgattt tgattctcaa acaaatgtgt  3780
cacaaagtaa ggattctgat gtgtatatca cagacaaatg tgtgctagac atgaggtcta  3840
tggacttcaa gagcaacagt gctgtggcct ggagcaacaa atctgacttt gcatgtgcaa  3900
acgccttcaa caacagcatt attccagaag acaccttctt ccccagccca gaaagttcct  3960
aataacctag gttaattaag aattcttta gaaggggata tacatatgaa aaaattatta  4020
ttcgcaattc ctttagttgt tccttttctat tctcacagcg cgcaggctgg tgtcactcag  4080
accccaaaat tccaggtcct gaagacagga cagagcatga cactgcagtg tgcccaggat  4140
atgaaccatg aatacatgtc ctggtatcga caagacccag catggggct gaggctgatt  4200 cattactcag ttggtgctgg tatcactgac caaggagaag tccccaatgg ctacaatgtc  4260
tccagatcaa ccacagagga tttcccgctc aggctgctgt cggctgctcc ctcccagaca  4320
tctgtgtact tctgtgccag cagttacgtc gggaacaccg gggagctgtt ttttggagaa  4380
ggctctaggc tgaccgtact ggaggacctg aaaaacgtgt tcccacccga ggtcgctgtg  4440
tttgagccat cagaagcaga gatctcccac acccaaaagg ccacactggt gtgcctggcc  4500
acaggcttct accccgacca cgtggagctg agctggtggg tgaatgggaa ggaggtgcac  4560
agtggggtct gcacagaccc gcagcccctc aaggagcagc ccgccctcaa tgactccaga  4620
tacgctctga gcagccgcct gagggtctcg gccaccttct ggcaggaccc ccgcaaccac  4680
ttccgctgtc aagtccagtt ctacgggctc tcggagaatg acgagtggac ccaggatagg  4740
```

```
gccaaacccg tcacccagat cgtcagcgcc gaggcctggg gtagagcaga cgcggccgca    4800
tctagacatc atcaccatca tcactagact gttgaaagtt gtttagcaaa accccataca    4860
gaaaattcat ttactaacgt ctggaaagac gacaaaactt tagatcgtta cgctaactat    4920
gagggttgtc tgtggaatgc tacaggcgtt gtagtttgta ctggtgacga aactcagtgt    4980
tacggtacat gggttcctat tgggcttgct atccctgaaa atgagggtgg tggctctgag    5040
ggtggcggtt ctgagggtgg cggttctgag ggtggcggta ctaaacctcc tgagtacggt    5100
gatacaccta ttccgggcta tacttatatc aaccctctcg acggcactta tccgcctggt    5160
actgagcaaa accccgctaa tcctaatcct tctcttgagg agtctcagcc tcttaatact    5220
ttcatgtttc agaataatag gttccgaaat aggcaggggg cattaactgt ttatacgggc    5280
actgttactc aaggcactga ccccgttaaa acttattacc agtacactcc tgtatcatca    5340
aaagccatgt atgacgctta ctggaacggt aaattcagag actgcgcttt ccattctggc    5400
tttaatgagg atccattcgt ttgtgaatat caaggccaat cgtctgacct gcctcaacct    5460
cctgtcaatg ctggcggcgg ctctggtggt ggttctggtg cggctctga gggtggtggc    5520 tctgagggtg gcggttctga gggtggcggc tctgaggag gcggttccgg tggtggctct    5580
ggttccggtg attttgatta tgaaaagatg gcaaacgcta ataagggggc tatgaccgaa    5640
aatgccgatg aaaacgcgct acagtctgac gctaaaggca aacttgattc tgtcgctact    5700
gattacggtg ctgctatcga tggtttcatt ggtgacgttt ccggccttgc taatggtaat    5760
ggtgctactg gtgattttgc tggctctaat tcccaaatgg ctcaagtcgg tgacggtgat    5820
aattcacctt taatgaataa tttccgtcaa tatttacctt ccctccctca atcggttgaa    5880 tgtcgcccctt tgtctttag cgctggtaaa ccatatgaat tttctattga ttgtgacaaa    5940
ataaacttat tccgtggtgt ctttgcgttt cttttatatg ttgccacctt tatgtatgta    6000
ttttctacgt ttgctaacat actgcgtaat aaggagtctt aataaggtac cctctagtca    6060
aggcctatag tgagtcgtat tacggactgg ccgtcgtttt acaacgtcgt gactgggaaa    6120
accctggcgt tacccaactt aatcgccttg cagcacatcc ccctttcgcc agctggcgta    6180
atagcgaaga ggcccgcacc gatcgccctt cccaacagtt gcgcagcctg aatggcgaat    6240
ggcgcttcgc ttggtaataa agcccgcttc ggcgggc                            6277
```

<210> SEQ ID NO 32
<211> LENGTH: 3383
<212> TYPE: DNA
<213> ORGANISM: Artificial Sequence
<220> FEATURE:
<223> OTHER INFORMATION: pEX821

<400> SEQUENCE: 32

```
gatctcgatc ccgcgaaatt aatacgactc actataggga gaccacaacg gtttccctct      60
agaaataatt ttgtttaact ttaagaagga gatatacata tgaacgctgg tgtcactcag     120
accccaaaat tccaggtcct gaagacagga cagagcatga cactgcagtg tgcccaggat     180
atgaaccatg aatacatgtc ctggtatcga caagacccag gcatgggct gaggctgatt     240 cattactcag ttggtgctgg tatcactgac caaggagaag tccccaatgg ctacaatgtc     300
tccagatcaa ccacagagga tttcccgctc aggctgctgt cggctgctcc ctcccagaca     360
tctgtgtact ctgtgccag caggcccgga ctagcgggag ggcgaccaga gcagtacttc     420
gggccgggca ccaggctcac ggtcacagag gacctgaaaa acgtgttccc acccgaggtc     480
```

```
gctgtgtttg agccatcaga agcagagatc tcccacaccc aaaaggccac actggtgtgc    540
ctggccaccg gtttctaccc cgaccacgtg gagctgagct ggtgggtgaa tgggaaggag    600
gtgcacagtg gggtctgcac agacccgcag cccctcaagg agcagcccgc cctcaatgac    660
tccagatacg ctctgagcag ccgcctgagg gtctcggcca ccttctggca ggaccccgc    720 aaccacttcc gctgtcaagt ccagttctac gggctctcgg agaatgacga gtggacccag    780
gatagggcca aacccgtcac ccagatcgtc agcgccgagg cctggggtag agcagactaa    840
gcttgaattc cgatccggct gctaacaaag cccgaaagga agctgagttg gctgctgcca    900
ccgctgagca ataactagca taaccccttg ggcctctaa acgggtcttg agggttttt    960 tgctgaaagg aggaactata tccggataat tcttgaagac gaaagggcct cgtgatacgc   1020
ctatttttat aggttaatgt catgataata atggtttctt agacgtcagg tggcactttt   1080
cggggaaatg tgcgcggaac ccctatttgt ttatttttct aaatacattc aaatatgtat   1140
ccgctcatga caataaacc ctgataaatg cttcaataat attttgttaa aattcgcgtt   1200
aaatttttgt taaatcagct cattttttaa ccaataggcc gaaatcggca aaatccctta   1260
taaatcaaaa gaatagaccg agatagggtt gagtgttgtt ccagtttgga acaagagtcc   1320
actattaaag aacgtggact ccaacgtcaa agggcgaaaa accgtctatc agggcgatgg   1380
cccactacgt gaaccatcac cctaatcaag ttttttgggg tcgaggtgcc gtaaagcact   1440
aaatcggaac cctaaaggga gcccccgatt tagagcttga cggggaaagc cggcgaacgt   1500
ggcgagaaag gaagggaaga agcgaaagg agcgggcgct agggcgctgg caagtgtagc   1560
ggtcacgctg cgcgtaacca ccacacccgc cgcgcttaat gcgccgctac agggcgcgtc   1620
aggtggcact tttcggggaa atgtgcgcgg aacccctatt tgtttatttt tctaaataca   1680
ttcaaatatg tatccgctca tgagacaata accctgataa atgcttcaat aatattgaaa   1740
aaggaagagt atgagtattc aacatttccg tgtcgccctt attcccttt ttgcggcatt   1800 ttgccttcct gttttgctc acccagaaac gctggtgaaa gtaaaagatg ctgaagatca   1860
gttgggtgca cgagtgggtt acatcgaact ggatctcaac agcggtaaga tccttgagag   1920
ttttcgcccc gaagaacgtt ttccaatgat gagcactttt aaagttctgc tatgtggcgc   1980
ggtattatcc cgtgttgacg ccgggcaaga gcaactcggt cgccgcatac actattctca   2040
gaatgacttg gttgagtact caccagtcac agaaaagcat cttacggatg gcatgacagt   2100
aagagaatta tgcagtgctg ccataaccat gagtgataac actgcggcca acttacttct   2160
gacaacgatc ggaggaccga aggagctaac cgcttttttg cacaacatgg gggatcatgt   2220
aactcgcctt gatcgttggg aaccggagct gaatgaagcc ataccaaacg acgagcgtga   2280
caccacgatg cctgcagcaa tggcaacaac gttgcgcaaa ctattaactg gcgaactact   2340
tactctagct tcccggcaac aattaataga ctggatggag gcggataaag ttgcaggacc   2400
acttctgcgc tcggcccttc cggctggctg gtttattgct gataaatctg gagccggtga   2460
gcgtgggtct cgcggtatca ttgcagcact ggggccagat ggtaagccct cccgtatcgt   2520
agttatctac acgacgggga gtcaggcaac tatggatgaa cgaaatagac agatcgctga   2580
gataggtgcc tcactgatta agcattggta actgtcagac caagtttact catatatact   2640
ttagattgat ttaaaacttc atttttaatt taaaaggatc taggtgaaga tcctttttga   2700
taatctcatg accaaaatcc cttaacgtga gttttcgttc cactgagcgt cagaccccgt   2760
agaaaagatc aaaggatctt cttgagatcc ttttttctg cgcgtaatct gctgcttgca   2820
aacaaaaaaa ccaccgctac cagcggtggt ttgtttgccg gatcaagagc taccaactct   2880
```

| | |
|---|---:|
| ttttccgaag gtaactggct tcagcagagc gcagatacca aatactgtcc ttctagtgta | 2940 |
| gccgtagtta ggccaccact tcaagaactc tgtagcaccg cctacatacc tcgctctgct | 3000 |
| aatcctgtta ccagtggctg ctgccagtgg cgataagtcg tgtcttaccg ggttggactc | 3060 |
| aagacgatag ttaccggata aggcgcagcg gtcgggctga acgggggggtt cgtgcacaca | 3120 |
| gcccagcttg gagcgaacga cctacaccga actgagatac ctacagcgtg agctatgaga | 3180 |
| aagcgccacg cttcccgaag ggagaaaggc ggacaggtat ccggtaagcg cagggtcgg | 3240 |
| aacaggagag cgcacgaggg agcttccagg gggaaacgcc tggtatcttt atagtcctgt | 3300 |
| cgggtttcgc cacctctgac ttgagcgtcg attttttgtga tgctcgtcag ggggcggag | 3360 |
| cctatggaaa aacgccagca acg | 3383 |

<210> SEQ ID NO 33
<211> LENGTH: 3342
<212> TYPE: DNA
<213> ORGANISM: Artificial Sequence
<220> FEATURE:
<223> OTHER INFORMATION: pEX954 Vector

<400> SEQUENCE: 33

| | |
|---|---:|
| gatctcgatc ccgcgaaatt aatacgactc actataggga gaccacaacg gtttccctct | 60 |
| agaaataatt ttgtttaact ttaagaagga gatataatcg atgtctaact cgagtgacaa | 120 |
| gtctgtctgc ctattcaccg attttgattc tcaaacaaat gtgtcacaaa gtaaggattc | 180 |
| tgatgtgtat atcacagaca aatgtgtgct agacatgagg tctatggact tcaagagcaa | 240 |
| cagtgctgtg gcctggagca acaaatctga ctttgcatgt gcaaacgcct tcaacaacag | 300 |
| cattattcca gaagacacct tcttccccag cccagaaagt tcctaagctt gaattccgat | 360 |
| ccggctgcta acaaagcccg aaaggaagct gagttggctg ctgccaccgc tgagcaataa | 420 |
| ctagcataac cccttggggc ctctaaacgg gtcttgaggg gttttttgct gaaggagga | 480 |
| actatatccg gataattctt gaagacgaaa gggcctcgtg atacgcctat ttttataggt | 540 |
| taatgtcatg ataataatgg tttcttagac gtgaggtggc acttttcggg gaaatgtgcg | 600 |
| cggaacccct atttgtttat ttttctaaat acattcaaat atgtatccgc tcatgagaca | 660 |
| ataaccctga taaatgcttc aataatattt tgttaaaatt cgcgttaaat ttttgttaaa | 720 |
| tcagctcatt ttttaaccaa taggccgaaa tcggcaaaat cccttataaa tcaaaagaat | 780 |
| agaccgagat agggttgagt gttgttccag tttggaacaa gagtccacta ttaaagaacg | 840 |
| tggactccaa cgtcaaaggg cgaaaaaccg tctatcaggg cgatggccca ctacgtgaac | 900 |
| catcacccta atcaagtttt tggggtcga ggtgccgtaa agcactaaat cggaaccta | 960 |
| aagggagccc ccgatttaga gcttgacggg gaaagccggc gaacgtggcg agaaaggaag | 1020 |
| ggaagaaagc gaaaggagcg ggcgctaggg cgctggcaag tgtagcggtc acgctgcgcg | 1080 |
| taaccaccac acccgccgcg cttaatgcgc cgctacaggg cgcgtcaggt ggcactttc | 1140 |
| ggggaaatgt gcgcggaacc cctatttgtt tattttttcta aatacattca aatatgtatc | 1200 |
| cgctcatgag acaataaccc tgataaatgc ttcaataata ttgaaaaagg aagagtatga | 1260 |
| gtattcaaca tttccgtgtc gcccttattc ccttttttgc ggcattttgc cttcctgttt | 1320 |
| ttgctcaccc agaaacgctg gtgaaagtaa aagatgctga agatcagttg ggtgcacgag | 1380 |
| tgggttacat cgaactggat ctcaacagcg gtaagatcct tgagagtttt cgccccgaag | 1440 |
| aacgttttcc aatgatgagc acttttaaag ttctgctatg tggcgcggta ttatcccgtg | 1500 |

```
ttgacgccgg gcaagagcaa ctcggtcgcc gcatacacta ttctcagaat gacttggttg    1560
agtactcacc agtcacagaa aagcatctta cggatggcat gacagtaaga gaattatgca    1620
gtgctgccat aaccatgagt gataacactg cggccaactt acttctgaca acgatcggag    1680
gaccgaagga gctaaccgct tttttgcaca acatggggga tcatgtaact cgccttgatc    1740
gttgggaacc ggagctgaat gaagccatac caaacgacga gcgtgacacc acgatgcctg    1800
cagcaatggc aacaacgttg cgcaaactat taactggcga actacttact ctagcttccc    1860
ggcaacaatt aatagactgg atggaggcgg ataaagttgc aggaccactt ctgcgctcgg    1920
cccttccggc tggctggttt attgctgata atctggagc cggtgagcgt gggtctcgcg    1980
gtatcattgc agcactgggg ccagatggta agccctcccg tatcgtagtt atctacacga    2040
cggggagtca ggcaactatg gatgaacgaa atagacagat cgctgagata ggtgcctcac    2100
tgattaagca ttggtaactg tcagaccaag tttactcata tatactttag attgatttaa    2160
aacttcattt ttaatttaaa aggatctagg tgaagatcct ttttgataat ctcatgacca    2220
aaatccctta acgtgagttt tcgttccact gagcgtcaga ccccgtagaa aagatcaaag    2280
gatcttcttg agatcctttt tttctgcgcg taatctgctg cttgcaaaca aaaaaaccac    2340
cgctaccagc ggtggtttgt ttgccggatc aagagctacc aactctttttt ccgaaggtaa    2400 ctggcttcag cagagcgcag ataccaaata ctgtccttct agtgtagccg tagttaggcc    2460
accacttcaa gaactctgta gcaccgccta catacctcgc tctgctaatc ctgttaccag    2520
tggctgctgc cagtggcgat aagtcgtgtc ttaccgggtt ggactcaaga cgatagttac    2580
cggataaggc gcagcggtcg ggctgaacgg ggggttcgtg cacacagccc agcttggagc    2640
gaacgaccta caccgaactg agatacctac agcgtgagct atgagaaagc gccacgcttc    2700
ccgaagggag aaaggcggac aggtatccgg taagcggcag ggtcggaaca ggagagcgca    2760
cgagggagct ccaggggga aacgcctggt atctttatag tcctgtcggg tttcgccacc    2820
tctgacttga gcgtcgattt tgtgatgct cgtcagggggg gcggagccta tggaaaaacg    2880
ccagcaacgc ggccttttta cggttcctgg cttttgctg ccttttgct cacatgttct    2940 ttcctgcgtt atcccctgat tctgtggata accgtattac cgcctttgag tgagctgata    3000
ccgctcgccg cagccgaacg accgagcgca gcgagtcagt gagcgaggaa gcggaagagc    3060
gcctgatgcg gtattttctc cttacgcatc tgtgcggtat ttcacaccgc aatggtgcac    3120
tctcagtaca atctgctctg atgccgcata gttaagccag tatacactcc gctatcgcta    3180
cgtgactggg tcatggctgc gccccgacac ccgccaacac ccgctgacgc gccctgacgg    3240
gcttgtctgc tcccggcatc cgcttacaga caagctgtga ccgtctccgg gagctgcatg    3300
tgtcagaggt tttcaccgtc atcaccgaaa cgcgcgaggc ag    3342
```

<210> SEQ ID NO 34
<211> LENGTH: 9
<212> TYPE: PRT
<213> ORGANISM: Homo sapiens

<400> SEQUENCE: 34

Ile Leu Ala Lys Phe Leu His Trp Leu
1               5

<210> SEQ ID NO 35
<211> LENGTH: 618
<212> TYPE: DNA
<213> ORGANISM: Artificial Sequence
<220> FEATURE:

-continued

<223> OTHER INFORMATION: DNA encoding the alpha chain of a soluble
DiS-linked ILA TCR

<400> SEQUENCE: 35

```
ggaatacaag tggagcagag tcctccagac ctgattctcc aggagggagc caattccacg     60
ctgcggtgca attttctga ctctgtgaac aatttgcagt ggtttcatca aaacccttgg    120
ggacagctca tcaacctgtt ttacattccc tcagggacaa acagaatgg aagattaagc    180
gccacgactg tcgctacgga acgctacagc ttattgtaca tttcctcttc ccagaccaca    240
gactcaggcg tttatttctg tgctgtggac tctgctacct caggaaccta caatacatc    300
tttggaacag gcaccaggct gaaggtttta gcaaatatcc agaaccctga ccctgccgtg    360
taccagctga gagactctaa atccagtgac aagtctgtct gcctattcac cgattttgat    420
tctcaaacaa atgtgtcaca agtaaggat tctgatgtgt atatcacaga caaatgtgtg    480
ctagacatga ggtctatgga cttcaagagc aacagtgctg tggcctggag caacaaatct    540
gactttgcat gtgcaaacgc cttcaacaac agcattattc cagaagacac cttcttcccc    600
agcccagaaa gttcctaa                                                 618
```

<210> SEQ ID NO 36
<211> LENGTH: 726
<212> TYPE: DNA
<213> ORGANISM: Artificial Sequence
<220> FEATURE:
<223> OTHER INFORMATION: DNA encoding the beta chain of a soluble
DiS-linked ILA TCR

<400> SEQUENCE: 36

```
aacgctggtg tcactcagac cccaaaattc caggtcctga agacaggaca gagcatgaca     60
ctgcagtgtg cccaggatat gaaccatgaa tacatgtcct ggtatcgaca agacccaggc    120
atggggctga ggctgattca ttactcagtt ggtgctggta tcactgacca aggagaagtc    180
cccaatggct acaatgtctc cagatcaacc acagaggatt tcccgctcag gctgctgtcg    240
gctgctccct cccagacatc tgtgtacttc tgtgccagca gttaccaagg cactgaagct    300
ttctttggac aaggcaccag actcacagtt gtagaggacc tgaaaacgt gttcccaccc    360
gaggtcgctg tgttttgagcc atcagaagca gagatctccc acacccaaaa ggccacactg    420
gtgtgcctgg ccacaggctt ctaccccgac cacgtggagc tgagctggtg ggtgaatggg    480
aaggaggtgc acagtggggt ctgcacagac ccgcagcccc tcaaggagca gcccgccctc    540
aatgactcca gatacgctct gagcagccgc ctgagggtct cggccacctt ctggcaggac    600
ccccgcaacc acttccgctg tcaagtccag ttctacgggc tctcggagaa tgacgagtgg    660
acccaggata gggccaaacc cgtcacccag atcgtcagcg ccgaggcctg ggtagagca    720
gactaa                                                              726
```

<210> SEQ ID NO 37
<211> LENGTH: 204
<212> TYPE: PRT
<213> ORGANISM: Artificial Sequence
<220> FEATURE:
<223> OTHER INFORMATION: Alpha chain of a soluble DiS-linked ILA TCR

<400> SEQUENCE: 37

```
Gly Ile Gln Val Glu Gln Ser Pro Pro Asp Leu Ile Leu Gln Glu Gly
1               5                   10                  15

Ala Asn Ser Thr Leu Arg Cys Asn Phe Ser Asp Ser Val Asn Asn Leu
            20                  25                  30
```

```
Gln Trp Phe His Gln Asn Pro Trp Gly Gln Leu Ile Asn Leu Phe Tyr
 35                  40                  45

Ile Pro Ser Gly Thr Lys Gln Asn Gly Arg Leu Ser Ala Thr Thr Val
 50                  55                  60

Ala Thr Glu Arg Tyr Ser Leu Leu Tyr Ile Ser Ser Gln Thr Thr
 65                  70                  75                  80

Asp Ser Gly Val Tyr Phe Cys Ala Val Asp Ser Ala Thr Ser Gly Thr
 85                  90                  95

Tyr Lys Tyr Ile Phe Gly Thr Gly Thr Arg Leu Lys Val Leu Ala Ile
100                 105                 110

Gln Asn Pro Asp Pro Ala Val Tyr Gln Leu Arg Asp Ser Lys Ser Ser
115                 120                 125

Asp Lys Ser Val Cys Leu Phe Thr Asp Phe Asp Ser Gln Thr Asn Val
130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
165                 170                 175

Asn Lys Ser Asp Phe Ala Cys Ala Asn Ala Phe Asn Asn Ser Ile Ile
180                 185                 190

Pro Glu Asp Thr Phe Phe Pro Ser Pro Glu Ser Ser
195                 200

<210> SEQ ID NO 38
<211> LENGTH: 241
<212> TYPE: PRT
<213> ORGANISM: Artificial Sequence
<220> FEATURE:
<223> OTHER INFORMATION: Beta chain of a soluble DiS-linked ILA TCR

<400> SEQUENCE: 38

Asn Ala Gly Val Thr Gln Thr Pro Lys Phe Gln Val Leu Lys Thr Gly
  1               5                  10                  15

Gln Ser Met Thr Leu Gln Cys Ala Gln Asp Met Asn His Glu Tyr Met
 20                  25                  30

Ser Trp Tyr Arg Gln Asp Pro Gly Met Gly Leu Arg Leu Ile His Tyr
 35                  40                  45

Ser Val Gly Ala Gly Ile Thr Asp Gln Gly Glu Val Pro Asn Gly Tyr
 50                  55                  60

Asn Val Ser Arg Ser Thr Thr Glu Asp Phe Pro Leu Arg Leu Leu Ser
 65                  70                  75                  80

Ala Ala Pro Ser Gln Thr Ser Val Tyr Phe Cys Ala Ser Ser Tyr Gln
 85                  90                  95

Gly Thr Glu Ala Phe Phe Gly Gln Gly Thr Arg Leu Thr Val Val Glu
100                 105                 110

Asp Leu Lys Asn Val Phe Pro Pro Glu Val Ala Val Phe Glu Pro Ser
115                 120                 125

Glu Ala Glu Ile Ser His Thr Gln Lys Ala Thr Leu Val Cys Leu Ala
130                 135                 140

Thr Gly Phe Tyr Pro Asp His Val Glu Leu Ser Trp Trp Val Asn Gly
145                 150                 155                 160

Lys Glu Val His Ser Gly Val Cys Thr Asp Pro Gln Pro Leu Lys Glu
165                 170                 175

Gln Pro Ala Leu Asn Asp Ser Arg Tyr Ala Leu Ser Ser Arg Leu Arg
180                 185                 190
```

```
Val Ser Ala Thr Phe Trp Gln Asp Pro Arg Asn His Phe Arg Cys Gln
195                 200                 205

Val Gln Phe Tyr Gly Leu Ser Glu Asn Asp Glu Trp Thr Gln Asp Arg
210                 215                 220

Ala Lys Pro Val Thr Gln Ile Val Ser Ala Glu Ala Trp Gly Arg Ala
225                 230                 235                 240

Asp

<210> SEQ ID NO 39
<211> LENGTH: 4
<212> TYPE: PRT
<213> ORGANISM: Homo sapiens

<400> SEQUENCE: 39

Ile Pro Ser Gly
1

<210> SEQ ID NO 40
<211> LENGTH: 6
<212> TYPE: PRT
<213> ORGANISM: Homo sapiens

<400> SEQUENCE: 40

Ser Val Gly Ala Gly Ile
1               5

<210> SEQ ID NO 41
<211> LENGTH: 6
<212> TYPE: PRT
<213> ORGANISM: Artificial Sequence
<220> FEATURE:
<223> OTHER INFORMATION: Mutated ILA TCR CDR2 Beta loop

<400> SEQUENCE: 41

Ser Ile His Pro Glu Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: Mutated ILA TCR CDR2 Beta loop

<400> SEQUENCE: 42

Ser Leu His Pro Ser Val
1               5

<210> SEQ ID NO 43
<211> LENGTH: 6
<212> TYPE: PRT
<213> ORGANISM: Artificial Sequence
<220> FEATURE:
<223> OTHER INFORMATION: Mutated ILA TCR CDR2 Beta loop

<400> SEQUENCE: 43

Ser Ile Cys Pro Ser Cys
1               5

<210> SEQ ID NO 44
<211> LENGTH: 6
<212> TYPE: PRT
<213> ORGANISM: Artificial Sequence
<220> FEATURE:
```

```
<223> OTHER INFORMATION: Mutated ILA TCR CDR2 Beta loop

<400> SEQUENCE: 44

Ser Ile Cys Trp Gly Cys
1               5

<210> SEQ ID NO 45
<211> LENGTH: 6
<212> TYPE: PRT
<213> ORGANISM: Artificial Sequence
<220> FEATURE:
<223> OTHER INFORMATION: Mutated ILA TCR CDR2 Beta loop

<400> SEQUENCE: 45

Ser Ile Trp Glu Phe Glu
1               5

<210> SEQ ID NO 46
<211> LENGTH: 6
<212> TYPE: PRT
<213> ORGANISM: Artificial Sequence
<220> FEATURE:
<223> OTHER INFORMATION: Mutated ILA TCR CDR2 Beta loop

<400> SEQUENCE: 46

Ser Arg Trp Val Gly Asp
1               5

<210> SEQ ID NO 47
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 47

Ile Met Pro Trp Gln Arg
1               5

<210> SEQ ID NO 48
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 48

Ile Gly Pro Tyr Gln Arg
1               5

<210> SEQ ID NO 49
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 49

Ile Gln Gly His Gln Arg
1               5

<210> SEQ ID NO 50
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop
```

-continued

<400> SEQUENCE: 50

Ile His Pro Trp Gln Arg
1               5

<210> SEQ ID NO 51
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 51

Ile Met Gly Trp Gln Arg
1               5

<210> SEQ ID NO 52
<211> LENGTH: 6
<212> TYPE: PRT
<213> ORGANISM: Artificial Sequence
<220> FEATURE:
<223> OTHER INFORMATION: Mutated 1G4 TCR CDR2 Alpha loop

<400> SEQUENCE: 52

Ile Pro Gly Trp Gln Arg
1               5

<210> SEQ ID NO 53
<211> LENGTH: 9
<212> TYPE: PRT
<213> ORGANISM: Homo sapiens

<400> SEQUENCE: 53

Ser Leu Tyr Asn Thr Val Ala Thr Leu
1               5

<210> SEQ ID NO 54
<211> LENGTH: 630
<212> TYPE: DNA
<213> ORGANISM: Artificial Sequence
<220> FEATURE:
<223> OTHER INFORMATION: DNA encoding the alpha chain of a soluble
      DiS-linked HIV Gag TCR

<400> SEQUENCE: 54
ccatcgatgg cccagaagga ggtggagcag aattctggac ccctcagtgt tccagaggga     60
gccattgcct ctctcaattg cacttacagt gaccgaggtt cccagtcctt cttctggtac    120
agacaatatt ctgggaaaag ccctgagttg ataatgttca tatactccaa tggtgacaaa    180
gaagatggaa ggtttacagc acagctcaat aaagccagcc agtatatttc cctgctcatc    240
agagactcca agctcagtga ttcagccacc tacctctgtg cggtgcgcac aaattccggg    300
tatgcactca acttcggcaa aggcacctcg ctgttggtca cacccatat ccagaaccct    360
gaccctgccg tgtaccagct gagagactct aagtcgagtg acaagtctgt ctgcctattc    420
accgattttg attctcaaac aaatgtgtca caaagtaagg attctgatgt gtatatcaca    480
gacaaatgtg tgctagacat gaggtctatg gacttcaaga gcaacagtgc tgtggcctgg    540
agcaacaaat ctgactttgc atgtgcaaac gccttcaaca acagcattat tccagaagac    600
accttcttcc ccagcccaga aagttcctaa                                     630

<210> SEQ ID NO 55
<211> LENGTH: 742

<212> TYPE: DNA
<213> ORGANISM: Artificial Sequence
<220> FEATURE:
<223> OTHER INFORMATION: DNA encoding the beta chain of a soluble
      DiS-linked HIV Gag TCR

<400> SEQUENCE: 55

```
tctctcatta atggaggctg gagtcacaca aagtcccaca cacctgatca aaacgagagg      60
acagcaagtg actctgagat gctctcctaa gtctgggcat gacactgtgt cctggtacca     120
acaggccctg ggtcaggggc cccagtttat ctttcagtat tatgaggagg aagagagaca     180
gagaggcaac ttccctgatc gattctcagg tcaccagttc cctaactata gctctgagct     240
gaatgtgaac gccttgttgc tgggggactc ggccctctat ctctgtgcca gcagcgacac     300
cgtctcctac gagcagtact tcgggccggg caccaggctc acggtcacag gacctgaa      360
aaacgtgttc ccacccgagg tcgctgtgtt tgagccatca gaagcagaga tctcccacac     420
ccaaaaggcc acactggtgt gcctggccac cggtttctac cccgaccacg tggagctgag     480
ctggtgggtg aatgggaagg aggtgcacag tggggtctgc acagacccgc agcccctcaa     540
ggagcagccc gccctcaatg actccagata cgctctgagc agccgcctga ggtctcggc      600
caccttctgg caggaccccc gcaaccactt ccgctgtcaa gtccagttct acgggctctc     660
ggagaatgac gagtggaccc aggatagggc caaacccgtc acccagatcg tcagcgccga     720
ggcctggggt agagcagact aa                                             742
```

<210> SEQ ID NO 56
<211> LENGTH: 207
<212> TYPE: PRT
<213> ORGANISM: Artificial Sequence
<220> FEATURE:
<223> OTHER INFORMATION: Alpha chain of a soluble DiS-linked HIV Gag
      TCR

<400> SEQUENCE: 56

```
Met Ala Gln Lys Glu Val Glu Gln Asn Ser Gly Pro Leu Ser Val Pro
1               5                   10                  15

Glu Gly Ala Ile Ala Ser Leu Asn Cys Thr Tyr Ser Asp Arg Gly Ser
            20                  25                  30

Gln Ser Phe Phe Trp Tyr Arg Gln Tyr Ser Gly Lys Ser Pro Glu Leu
        35                  40                  45

Ile Met Phe Ile Tyr Ser Asn Gly Asp Lys Glu Asp Gly Arg Phe Thr
    50                  55                  60

Ala Gln Leu Asn Lys Ala Ser Gln Tyr Ile Ser Leu Leu Ile Arg Asp
65                  70                  75                  80

Ser Lys Leu Ser Asp Ser Ala Thr Tyr Leu Cys Ala Val Arg Thr Asn
                85                  90                  95

Ser Gly Tyr Ala Leu Asn Phe Gly Lys Gly Thr Ser Leu Leu Val Thr
            100                 105                 110

Pro His Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
```

```
                180                 185                 190
Ser Ile Ile Pro Glu Asp Thr Phe Phe Pro Ser Pro Glu Ser Ser
195                 200                 205
```

<210> SEQ ID NO 57
<211> LENGTH: 243
<212> TYPE: PRT
<213> ORGANISM: Artificial Sequence
<220> FEATURE:
<223> OTHER INFORMATION: Beta chain of a soluble DiS-linked HIV Gag TCR

<400> SEQUENCE: 57

```
Met Glu Ala Gly Val Thr Gln Ser Pro Thr His Leu Ile Lys Thr Arg
1               5                   10                  15

Gly Gln Gln Val Thr Leu Arg Cys Ser Pro Lys Ser Gly His Asp Thr
            20                  25                  30

Val Ser Trp Tyr Gln Gln Ala Leu Gly Gln Gly Pro Gln Phe Ile Phe
        35                  40                  45

Gln Tyr Tyr Glu Glu Glu Arg Gln Arg Gly Asn Phe Pro Asp Arg
50                  55                  60

Phe Ser Gly His Gln Phe Pro Asn Tyr Ser Ser Glu Leu Asn Val Asn
65                  70                  75                  80

Ala Leu Leu Leu Gly Asp Ser Ala Leu Tyr Leu Cys Ala Ser Ser Asp
            85                  90                  95

Thr Val Ser Tyr Glu Gln Tyr Phe Gly Pro Gly Thr Arg Leu Thr Val
        100                 105                 110

Thr Glu Asp Leu Lys Asn Val Phe Pro Pro Glu Val Ala Val Phe Glu
    115                 120                 125

Pro Ser Glu Ala Glu Ile Ser His Thr Gln Lys Ala Thr Leu Val Cys
130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
            165                 170                 175

Lys Glu Gln Pro Ala Leu Asn Asp Ser Arg Tyr Ala Leu Ser Ser Arg
        180                 185                 190

Leu Arg Val Ser Ala Thr Phe Trp Gln Asp Pro Arg Asn His Phe Arg
    195                 200                 205

Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Asp
```

<210> SEQ ID NO 58
<211> LENGTH: 5
<212> TYPE: PRT
<213> ORGANISM: Homo sapiens

<400> SEQUENCE: 58

```
Ile Tyr Ser Asn Gly
1               5
```

<210> SEQ ID NO 59
<211> LENGTH: 6
<212> TYPE: PRT
<213> ORGANISM: Homo sapiens

-continued

```
<400> SEQUENCE: 59

Tyr Tyr Glu Glu Glu Glu
1               5

<210> SEQ ID NO 60
<211> LENGTH: 6
<212> TYPE: PRT
<213> ORGANISM: Artificial Sequence
<220> FEATURE:
<223> OTHER INFORMATION: Mutated HIV Gag TCR CDR2 Beta loop

<400> SEQUENCE: 60

Tyr Val Arg Gly Val Glu
1               5

<210> SEQ ID NO 61
<211> LENGTH: 6
<212> TYPE: PRT
<213> ORGANISM: Artificial Sequence
<220> FEATURE:
<223> OTHER INFORMATION: Mutated HIV Gag TCR CDR2 Beta loop

<400> SEQUENCE: 61

Tyr Ala Leu Gly Glu Glu
1               5
```